United States Patent
Jacobsen et al.

(12) 
(10) Patent No.: US 6,586,592 B2
(45) Date of Patent: Jul. 1, 2003

(54) BIS-ARYLSULFONES

(75) Inventors: Eric Jon Jacobsen, Richland, MI (US); Stephen J. King, Portage, MI (US); Kalpana M. Merchant, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 21 days.

(21) Appl. No.: 09/969,306

(22) Filed: Oct. 2, 2001

(65) Prior Publication Data

US 2002/0115660 A1 Aug. 22, 2002

Related U.S. Application Data

(63) Continuation-in-part of application No. 09/877,308, filed on Jun. 8, 2001.
(60) Provisional application No. 60/212,894, filed on Jun. 20, 2000, provisional application No. 60/237,025, filed on Sep. 29, 2000, provisional application No. 60/239,713, filed on Oct. 12, 2000, and provisional application No. 60/268,261, filed on Feb. 13, 2001.

(51) Int. Cl.[7] .................. C07D 243/08; G06K 9/00; A61B 5/055; A61K 49/04
(52) U.S. Cl. ................. 540/575; 382/131; 424/9.37; 424/9.44
(58) Field of Search ........................ 540/575

(56) References Cited

U.S. PATENT DOCUMENTS

| | | | |
|---|---|---|---|
| 4,851,423 A | 7/1989 | Girijavallabhan et al. | 514/399 |
| 5,627,077 A | 5/1997 | Dyllick-Brenzinger et al. | 436/106 |
| 6,130,215 A | 10/2000 | Jakoczi et al. | 514/252 |

FOREIGN PATENT DOCUMENTS

| | | |
|---|---|---|
| JP | 3056-431 A | 6/1989 |
| JP | 07033735 A | 7/1993 |
| WO | WO 92/06683 | 4/1992 |
| WO | WO 9408956 A1 | 10/1992 |
| WO | WO 92/20642 | 11/1992 |
| WO | WO 93/17682 | 9/1993 |
| WO | WO 93/18035 | 9/1993 |
| WO | WO 97/07790 | 3/1997 |
| WO | WO 99/02502 | 1/1999 |
| WO | WO 99/37623 | 7/1999 |
| WO | WO 99/42465 | 8/1999 |
| WO | WO 99/47516 | 9/1999 |
| WO | WO 00 12623 | 3/2000 |

OTHER PUBLICATIONS

RA Glennon, "Serotonin Receptors: Clinical Implications," Neuroscience & Behavioral Reviews 14:35–47 (1990).
D Hoyer et al., "International Union of Pharmacology classification of receptors for 5–hydroxytryptamine (Serotonin)," Pharmacological Reviews 46(2):157–203 (1994); [Abstract of].
FJ Monsma, et al., "Cloning and expression of a novel serotonin receptor with high affinity for tricyclic psychotropic drugs," American Society for Pharmacology and Experimental Therapeutics 43(3):320–327; [Abstract of] 1993.
M. Ruat. et al., "A Novel Rat Serotonin ($5-HT_6$) receptor: Molecular Cloning, Localization and Stimulation of cAMP Accumulation," Biochemical and Biophysical Research Communications 193(1):268–276 (1993).
BL Roth et al., "Binding of typical and atypical antipsychotic agents to 5–hydroxytryptamine–6 and 5–hydroxytryptamine–7 receptors," American Society for Pharmacology and Experimental Therapeutics 268(3):1403–1410 (1994).
AJ Sleight et al., "The 5–HT6 receptor: localization and function," 8:1217–1224 (1998); [Abstract of].
A Bourson et al., "Involvement of 5–HT6 receptors in nigrostriatal function in rodents," British Journal of Pharmacology 125:1562–1566; [Abstract of] 1998.
FG Boess, et al., "The 5–Hydroxytryptamine$_6$ Receptor–Selective radioligand [$^3$H]Ro 63–0563 Labels 5–Hydroxytryptamine Receptor Binding Sites in Rat and Porcine Striatum," Molecular Pharmacology 54(3):577–583 (1998).
AJ Sleight et al., "Characterization of Ro 04–6790 and Ro 63–0563: potent and selective antagonists at human and rat 5–HT6 receptors," British Journal of Pharmacology 124(3):556–562 (1998); [Abstract of].
M. Yoshioka et al., "Central Distribution and Function of $5-HT_6$ Receptor Subtype in the Rat Brain," Life Sciences 62(17/18):1473–1477 (1998).

*Primary Examiner*—Brenda Coleman
(74) *Attorney, Agent, or Firm*—Mary J. Hosley

(57) ABSTRACT

The present invention provides pharmaceutically active compounds useful for the treatment of diseases or disorders of the central nervous system.

4 Claims, No Drawings

BIS-ARYLSULFONES

CROSS REFERENCE TO RELATED APPLICATIONS

This application is a continuation-in-part of U.S. Ser. No. 09/877,308, filed Jun. 8, 2001, which claims the benefit of the following provisional applications: U.S. Serial No. 60/212,894, filed Jun. 20, 2000; U.S. Serial No. 60/237,025, filed Sep. 29, 2000; U.S. No. 60/239,713, filed Oct. 12, 2000; and U.S. Serial No. 60/268,261, filed Feb. 13, 2001, under 35 USC 119(e)(1).

FIELD OF THE INVENTION

The present invention relates to novel bis-arylsulfone derivatives, and more specifically, relates to bis-arylsulfone compounds of formula I described herein below. These compounds are 5-HT receptor ligands and are useful for treating diseases wherein modulation of 5-HT activity is desired.

BACKGROUND OF THE INVENTION

Serotonin has been implicated in a number of diseases and conditions that originate in the central nervous system. These include diseases and conditions related to sleeping, eating, perceiving pain, controlling body temperature, controlling blood pressure, depression, anxiety, schizophrenia, and other bodily states. Serotonin also plays an important role in peripheral systems, such as the gastrointestinal system, where it has been found to mediate a variety of contractile, secretory, and electrophysiologic effects.

As a result of the broad distribution of serotonin within the body, there is a tremendous interest in drugs that affect serotonergic systems. In particular, agonists, partial agonists and antagonists are of interest for the treatment of a wide range of disorders, including anxiety, depression, hypertension, migraine, obesity, compulsive disorders, schizophrenia, autism, neurodegenerative disorders (e.g. Alzheimer's disease, Parkinsonism, and Huntington's chorea), and chemotherapy-induced vomiting.

The major classes of serotonin receptors ($5-HT_{1-7}$) contain fourteen to eighteen separate receptors that have been formally classified. See Glennon, et al., Neuroscience and Behavioral Reviews, 1990, 14, 35; and D. Hoyer, et al. Pharmacol. Rev. 1994, 46, 157–203.

There is currently a need for pharmaceutical agents that are useful to treat diseases and conditions that are associated with 5-HT receptors. In particular, there is a need for agents that can selectively bind to individual receptor subtypes (e.g. receptor-specific agonists or antagonists); such agents would be useful as pharmaceutical agents, or would be useful to facilitate the study of the 5-HT receptor family, or to aid in the identification of other compounds that selectively bind to the specific 5-HT receptors.

For example, The $5-HT_6$ receptor is identified in 1993 (Monsma et al. Mol. Pharmacol. 1993, 43, 320–327 and Ruat, M. et al. Biochem. Biophys. Res. Com. 1993, 193, 269–276). Several antidepressants and atypical antipsychotics bind to the $5-HT_6$ receptor with high affinity and this binding may be a factor in their profile of activities (Roth et al. J. Pharm. Exp. Therapeut. 1994, 268, 1403–1410; Sleight et al. Exp. Opin. Ther. Patents 1998, 8, 1217–1224; Bourson et al. Brit. J. Pharm. 1998, 125, 1562–1566; Boess et al. Mol. Pharmacol. 1998, 54, 577–583; Sleight et al. Brit. J. Pharmacol. 1998, 124, 556–562). In addition, the $5-HT_6$ receptor has been linked to generalized stress and anxiety states (Yoshioka et al. Life Sciences 1998, 17/18, 1473–1477). Together these studies and observations suggest that compounds that antagonize the $5-HT_6$ receptor will be useful in treating disorders of the central nervous system.

Generally, compounds of the present invention are 5-HT ligands. In particular, they can selectively bind to the $5-HT_6$ receptor (e.g. receptor-specific agonists or antagonists). Thus, they are useful for treating diseases wherein modulation of 5-HT activity, specifically $5-HT_6$ activity, is desired. Therefore, the compounds of this invention are useful for the treatment of diseases or disorders of the central nervous system. More specifically, for the treatment of psychosis, paraphrenia, psychotic depression, mania, schizophrenia, schizophreniform disorders, anxiety, migraine headache, drug addiction, convulsive disorders, personality disorders, post-traumatic stress syndrome, alcoholism, panic attacks, obsessive-compulsive disorders, and sleep disorders. The compounds of this invention are also useful to treat psychotic, affective, vegetative, and psychomotor symptoms of schizophrenia and the extrapyramidal motor side effects of other antipsychotic drugs. This last action will allow higher doses of antipsychotics to be used and thus greater antipsychotic efficacy to be obtained as a result of a reduction in side effects. The compounds of this invention are also useful in the modulation of eating behavior and thus are useful in treating excess weight and associated morbidity and mortality.

INFORMATION DISCLOSURE

U.S. Pat. No. 5,627,077 discloses aniline compounds useful in making mineral oils.

U.S. Pat. No. 4,851,423 discloses pharmaceutically active compounds having antiviral and antiinflammatory.

PCT International Publication WO 99/37623 discloses novel compounds having pharmacological activity for the treatment of CNS disorders.

PCT International Publication WO 99/47516 discloses 3-(2-pyrrolidinylmethyl)-indole compound having 5-HT6 affinity.

PCT International Publication WO 99/42465 discloses novel sulphonamide derivatives having CNS activity.

PCT International Publication WO 99/02502 discloses novel compounds having pharmacological activity for the treatment of CNS disorders.

PCT International Publication WO 93/17682 discloses angiotensin II receptor antagonists.

PCT International Publication WO 92/06683 discloses pharmaceutical compositions having anti-retrovirus activity.

PCT International Publication WO 92/20642 discloses bis or mono bicyclic aryl and/or heteroaryl compounds exhibiting protein tyrosine kinase inhibition activity.

Abstract of PCT International Publication WO 92/9408956A discloses compounds useful for depress blood lipid levels.

Abstract of JO 3056-431-a discloses diphenyl compounds having analgesic, anti-inflammatory, anti-rheumatic, and anti-nephritic activity.

Abstract of JP 07033735-A discloses diphenyl-sulphone compounds useful for treating inflammation, allergies and asthma.

Abstract of WO 9318035 discloses angiotensin II receptor containing fused heterocycle and two phenyl rings.

Abstract of WO 9707790 discloses compounds containing diphenyl for treating infectious infectious diseases such as malaria.

SUMMARY OF THE INVENTION

The present invention provides novel compounds of formula I:

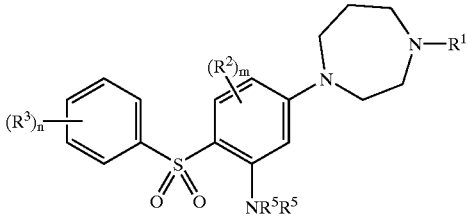

Or a pharmaceutically acceptable salt thereof wherein $R^1$ is H, $C_{1-12}$ alkyl, $C_{1-6}$ alkylaryl, or aryl; each $R^2$ is independently H, $C_{1-12}$ alkyl, $C_{1-12}$ alkenyl, halo, $NO_2$, CN, $CF_3$, or $OR^1$; each $R^3$ is independently H, $C_{1-12}$ alkyl, $C_{1-12}$ alkenyl, or $R^4$; $R^4$ is halo, $NO_2$, CN, $CF_3$, $OR^1$, CON $R^1R^1$, $NHSO_2R^1$, $NR^1R^1$, $NR^1COR^1$, $SO_2N\ R^1R^1$, $C(=O)R^1$, $CO_2R^1$, or $S(O)_iR^1$; each $R^5$ is independently H, $C_{1-6}$ alkyl, $C_{1-6}$ alkylaryl, aryl, $C(=O)R^1$, $S(O)_2R^1$, $C(O)NR^1R^1$, $CO_2R^1$, or $CSR^1$; at each occurrence, alkyl, alkenyl, alkyaryl or aryl is optionally substituted with one or more $R^4$;

i is 0, 1, or 2; m is 1, 2 or 3; and n is 1, 2, 3, 4, or 5.

The present invention further provides novel compounds of formula II:

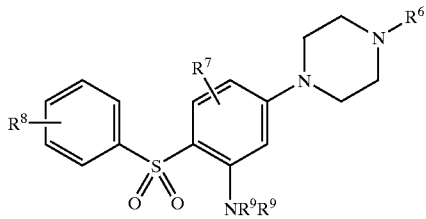

Or a pharmaceutically acceptable salt thereof wherein $R^6$ is H, or $C_{1-4}$ alkyl; $R^7$ is H, halo, $C_{1-4}$ alkyl, or $NR^6R^6$; $R^8$ is H, halo, or $C_{1-4}$ alkyl; and; each $R^9$ is independently H, $C_{1-4}$ alkyl, $C(=O)R^{10}$, $S(O)_2R^{10}$, $C(O)NR^{10}R^{10}$, $CO_2R^{10}$, or $CSR^{10}$; and each $R^{10}$ is independently H, $C_{1-12}$ alkyl, $C_{1-6}$ alkylaryl, or aryl.

The present invention further provides a pharmaceutical composition comprising a compound of formula I or II, or a pharmaceutically acceptable salt thereof, and a pharmaceutically acceptable carrier. In preferred embodiments, the composition preferably comprises a therapeutically effective amount of a compound of formula I or a pharmaceutically acceptable salt thereof.

The present invention further provides a method for treating a disease or condition in a mammal wherein a 5-HT receptor is implicated and modulation of a 5-HT function is desired comprising administering to the mammal a therapeutically effective amount of a compound of formula III

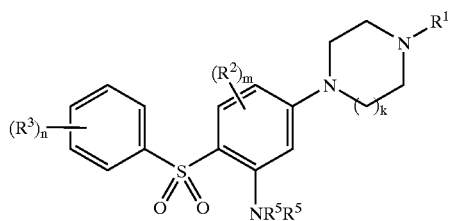

or a pharmaceutically acceptable salt thereof wherein
$R^1$ is H, $C_{1-12}$ alkyl, $C_{1-6}$ alkylaryl, or aryl; each $R^2$ is independently H, $C_{1-12}$ alkyl, $C_{1-12}$ alkenyl, halo, $NO_2$, CN, $CF_3$, or $OR^1$; each $R^3$ is independently H, $C_{1-12}$ alkyl, $C_{1-12}$ alkenyl, or $R^4$; $R^4$ is halo, $NO_2$, CN, $CF_3$, $OR^1$, CON $R^1R^1$, $NHSO_2R^1$, $NR^1R^1$, $NR^1COR^1$, $SO_2N\ R^1R^1$, $C(=O)R^1$, $CO_2R^1$, or $S(O)_iR^1$; each $R^5$ is independently H, $C_{1-6}$ alkyl, $C_{1-6}$ alkylaryl, aryl, $C(=O)R^1$, $S(O)_2R^1$, $C(O)NR^1R^1$, $CO_2R^1$, or $CSR^1$; at each occurrence, alkyl, alkenyl, alkyaryl or aryl is optionally substituted with one or more $R^4$; k is 1 or 2; i is 0, 1, or 2; m is 1, 2 or 3; and n is 1, 2, 3, 4, or 5.

The compounds of formulae I, II, and III also can include isotopic labels. For example the compounds 5-(1,4-diazepan-1-yl)-2-[(3-fluorophenyl) sulfonyl]phenylamine; 5-(1,4-diazepan-1-yl)-N-ethyl-2-[(3-fluorophenyl) sulfonyl] aniline; N-[5-(1,4-diazepan-1-yl)-2-[(3-fluorophenyl) sulfonyl]phenyl]acetamide; N-[5-(1,4-diazepan-1-yl)-2-[phenylsulfonyl]phenyl]acetamide, and pharmaceutically acceptable salts thereof may contain an isotopic label such as at least on atom selected from Carbon-11, Nitrogen-13, Oxygen-15, and Fluorine-18. Isotopically labeled compounds may be used in positron emission tomography.

In other embodiments, the compounds 5-(1,4-diazepan-1-yl)-2-[(3-fluorophenyl) sulfonyl]phenylamine; 5-(1,4-diazepan-1-yl)-N-ethyl-2-[(3-fluorophenyl) sulfonyl] aniline; N-[5-(1,4-diazepan-1-yl)-2-[(3-fluorophenyl) sulfonyl]phenyl]acetamide; and pharmaceutically acceptable salts thereof, each containing at least one $^{19}F$ atom, may be used in nuclear magnetic resonance imaging.

The present invention further provides a method for treating a disease or condition in a mammal wherein a 5-HT$_6$ receptor is implicated and modulation of a 5-HT$_6$ function is desired comprising administering to the mammal a therapeutically effective amount of a compound of formula III, or a pharmaceutically acceptable salt thereof.

The present invention further provides a method for treating or preventing diseases or disorders of the central nervous system comprising administering a therapeutically effective amount of a compound of formula III, or a pharmaceutically acceptable salt thereof to the mammal. Diseases or disorders for which a compound of formula I may have activity include, but are not limited to the following: obesity, depression, schizophrenia, schizophreniform disorder, schizoaffective disorder, delusional disorder, a stress related disease (e.g. general anxiety disorder), panic disorder, a phobia, obsessive compulsive disorder, post-traumatic-stress syndrome, immune system depression, major depression, a stress induced problem with the urinary, gastrointestinal or cardiovascular system (e.g., stress incontinence), neurodegenerative disorders, autism, chemotherapy-induced vomiting, hypertension, migraine headaches, cluster headaches, sexual dysfunction in a mammal (e.g. a human), addictive disorder and withdrawal syndrome, an adjustment disorder, an age-associated learning and mental disorder, anorexia nervosa, apathy, an attention-deficit disorder due to general medical conditions, attention-deficit hyperactivity disorder, behavioral disturbance (including agitation in conditions associated with diminished cognition (e.g., dementia, mental retardation or delirium)), bipolar disorder, bulimia nervosa, chronic fatigue syndrome, conduct disorder, cyclothymic disorder, dysthymic disorder, fibromyalgia and other somatoform disorders, generalized anxiety disorder, an inhalation disorder, an intoxication disorder, movement disorder (e.g., Huntington's disease or Tardive Dyskinesia), oppositional defiant disorder, peripheral neuropathy, post-traumatic stress disorder, premenstrual dysphoric disorder, a psychotic disorder (brief and long duration disorders, psychotic disorder due to medical condition, psychotic disorder NOS), mood disorder (major depressive or bipolar disorder with psychotic features) seasonal affective disorder, a sleep disorder, cognitive disorders, iritable bowel syndrome, a specific developmental disorder, agitation disorder, selective serotonin reuptake inhibition (SSRI) "poop out" syndrome or a Tic disorder (e.g., Tourette's syndrome).

The present invention further provides a method for treating anxiety, or stress related disorders comprising administering a therapeutically effective amount of a compound of formula III, or a pharmaceutically acceptable salt thereof to the mammal.

The present invention further provides a method for treating depression comprising administering a therapeutically effective amount of a compound of formula III, or a pharmaceutically acceptable salt thereof to the mammal.

The present invention further provides a method for treating obesity comprising administering a therapeutically effective amount of a compound of formula III, or a pharmaceutically acceptable salt thereof to the mammal.

The present invention further provides the use of a compound of formula III or a pharmaceutically acceptable salt thereof to prepare a medicament for treating or preventing diseases or disorders of the central nervous system.

The present invention further provides a composition of formula I and a pharmaceutically acceptable carrier.

The present invention further provides a composition of formula II and a pharmaceutically acceptable carrier.

The invention may also provide novel intermediates and processes for preparing compounds of formula III.

DETAILED DESCRIPTION OF THE INVENTION

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours, "rt" for room temperature, and etc.).

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

Specific and preferred values listed below for radicals, groups, moieties, substituents, or ranges, are for illustration only; they do not exclude other defined values or other values within defined ranges.

The following definitions are used, unless otherwise described.

The term "halo" denotes fluoro, chloro, bromo, or iodo.

Alkyl denotes both straight and branched groups; but reference to an individual group or moiety such as "propyl" embraces only the straight chain group or moiety, a branched chain isomer such as "isopropyl" being specifically referred to.

Aryl denotes a phenyl radical or an ortho-fused bicyclic carbocyclic group or moiety having about nine to ten ring atoms in which at least one ring is aromatic.

Mammal denotes human and animals.

It is to be understood that the present invention encompasses any racemic, optically-active, polymorphic, tautomeric, or stereoisomeric form, or mixture thereof, of a compound of the invention, which possesses the useful properties described herein.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, maleate, fumarate, benzenesulfonate and α-glycerophosphate. Suitable inorganic salts may also be formed, including hydrobromide, hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

In one embodiment, $R^1$ is H or $C_{1-4}$alkyl.

In another embodiment, $R^1$ is methyl.

In one embodiment, $R^1$ is H.

In another embodiment, each $R^2$ is independently H or $C_{1-6}$alkyl.

In another embodiment, $R^2$ is H.

In one embodiment, each $R^3$ is independently H, fluoro or $C_{1-4}$alkyl.

In one embodiment, each $R^3$ is fluoro, n is one or two.

In one embodiment, each $R^5$ is H independently or $C_{1-4}$alkyl.

In one embodiment, $R^5$ is H.

In one embodiment, each $R^5$ is independently H, or $C(=O)R^1$.

In one embodiment, each $R^5$ is independently H, or $C(=O)RCH_3$.

In one embodiment, each $R^5$ is independently H, $S(O)_2R^1$, $C(O)NR^1R^1$, $CO_2R^1$, or $CSR^1$.

In one embodiment, $R^6$ is H, methyl or ethyl.

In one embodiment, $R^7$ is H.

In one embodiment, $R^8$ is H or fluoro, or methyl.

Examples of the present invention are:
(1) 5-(1,4-diazepan-1-yl)-2-[(3-fluorophenyl)sulfonyl] phenylamine,
(2) 5-(1,4-diazepan-1-yl)-2-[(3,4-difluorophenyl)sulfonyl] phenyl amine,
(3) 5-(1,4-diazepan-1-yl)-2-(phenylsulfonyl)phenylamine,
(4) 5-(1,4-diazepan-1-yl)-2-[(3,5-difluorophenyl)sulfonyl] phenylamine,
(5) 5-(1,4-diazepan-1-yl)-2-[(3-fluorophenyl)sulfonyl]-N-methylphenyl amine, (6) 5-(1,4-diazepan-1-yl)-N-ethyl-2-[(3-fluorophenyl) sulfonyl]aniline,
(7) 5-(1,4-diazepan-1-yl)-N,N-diethyl-2-[(3-fluorophenyl) sulfonyl]phenylamine,
(8) N-[5-(1,4-diazepan-1-yl)-2-(phenylsulfonyl) phenyl] acetamide,
(9) N-[2-[(3-fluorophenyl)sulfonyl]-5-(4-methyl-1,4-diazepan-1-yl)phenyl]acetamide, or
(10) N-[5-(1,4-diazepan-1-yl)-2-[(3-fluorophenyl) sulfonyl] phenyl]-N-ethylacetamide, or a pharmaceutically acceptable salt thereof.

Another examples of the present invention are:
(1) 2-(phenylsulfonyl)-5-(1-piperazinyl)phenylamine,
(2) 2-[(4-fluorophenyl)sulfonyl]-5-(1-piperazinyl) phenylamine,
(3) 2-[(4-fluorophenyl)sulfonyl]-5-(4-methyl-1-piperazinyl) phenylamine,
(4) 2-[(4-methylphenyl)sulfonyl]-5-(1-piperazinyl) phenylamine,
(5) 2-[(4-methylphenyl)sulfonyl]-5-(4-methyl-1-piperazinyl)phenylamine,
(6) 5-(4-methyl-1-piperazinyl)-2-(phenylsulfonyl) phenylamine,
(7) 2-[(3-fluorophenyl)sulfonyl]-5-(4-methyl-1-piperazinyl) phenylamine, or
(8) N-ethyl-2-(phenylsulfonyl)-5-(1-piperazinyl) phenylamine, or a pharmaceutically acceptable salt thereof.

Specific example of the present invention is N-[5-(1,4-diazepan-1-yl)-2-[(3-fluorophenyl)sulfonyl]phenyl] acetamide, or its pharmaceutically acceptable salt thereof.

Specific example of the present invention is 5-(1,4-diazepan-1-yl)-2-(phenylsulfonyl) phenylamine, or its pharmaceutically acceptable salt thereof.

Specific example of the present invention is N-[5-(1,4-diazepan-1-yl)-2-(phenylsulfonyl) phenyl]acetamide, or its pharmaceutically acceptable salt thereof.

Chart I and Chart II describe the preparation of compounds of the present invention. All of the starting materials are prepared by procedures described herein or by procedures that would be well known to one of ordinary skill in organic chemistry. As shown in Chart I, treatment of commercially available substituted or unsubstituted 2,5-difluoronitro-benzene 1 with the desired arylthiol gave thioether 2. This reaction is usually carried out in the presence of a suitable base such as potassium carbonate and a suitable solvent such as acetonitrile. The oxidation of 2 to sulfone 3 is usually carried out using m-CPBA (in $CH_2Cl_2$) or $H_2O_2$ (in hot acetic acid) as the oxidizing agents. When using m-CPBA, the reaction is done at ambient temperature in a solvent such as $CH_2Cl_2$. The desired arylpiperazine moiety 4 is formed by a second nucleophilic substitution reaction, using the appropriate amine. Again, this displacement is done using potassium carbonate as the base and a solvent such as acetonitrile. Depending on the $R^1$-substituent, reduction of nitrobenzene 4 to the aniline 5 is accomplished using Raney nickel and hydrazine. The solvent system most typically utilized is EtOH/THF. If further purification of 5 is desired, piperazine 4 is protected as the tert-butyl carbamate using di-tert-butyl dicarbonate (THF, $H_2O$) to give carbamate 6. This compound is reduced as described above using Raney Nickel, to give aniline 7. In contrast to compound 5, carbamate 7 can be readily purified by chromatography. Deprotection using TFA in $CH_2Cl_2$ provided bis-sulfone 5. If desired, carbamate 7 can be alkylated to give compound of structure 8. In this case, treatment of 7 with methyltriflate in the presence of potassium hydride gives the methylamine 8. Deprotection, as described above, using TFA in $CH_2Cl_2$ provides a compound of structure 5.

Alternatively, N-alkylated compound of structure 5 can be prepared according to CHART II as shown here. Reaction of a compound of structure 2 with a desired piperazine, as decribed in Chart I (potassium carbonate/acetonitrile; at ambient to elevated temperatures), provideds piperazine 9. Protection of 9 using di-tert-butyl dicarbonate provided carbamate 10. Reduction of nitro 10 using Raney nickel and hydrazine gives aniline 11, which can be readily reacted with acetyl chloride to give 12. This reaction is carried out quite effectively using acetyl chloride (or other acyl chlorides or ethyl formate), in the presence of DMAP, and Hunigs base, in a suitable solvent such as $CH_2Cl_2$. Oxidation of 12 to the sulfone is accomplished with m-CPBA ($CH_2Cl_2$, $-78°$ C.-rt) to give 13. Reduction of amide 13 utilizing boranemethylsulfide complex gives the desired alkylamine 14. The piperazine is the deprotected and alkylated to provide a compound of structure 5. If desired, a dialkylated compound can also be prepared according to the methods well-known in the art. If desired, amides such as 13 in Chart II may be simply deprotected using either TFA, HCl in EthOH, or TsOH to give acetamide 5 ($R5=COCH_3$). Sulfonamides can be prepared in a similar fashion.

CHART I

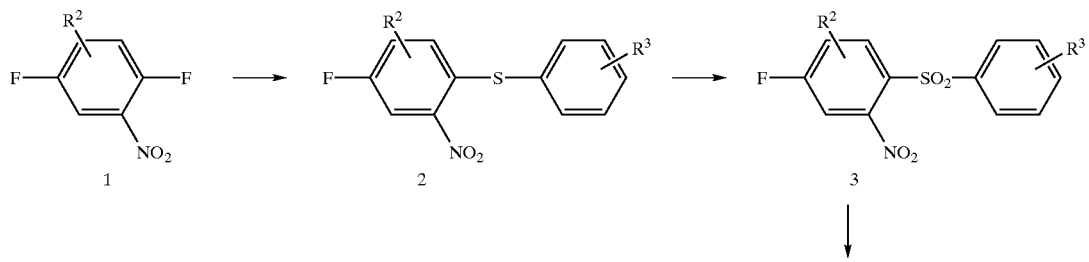

-continued
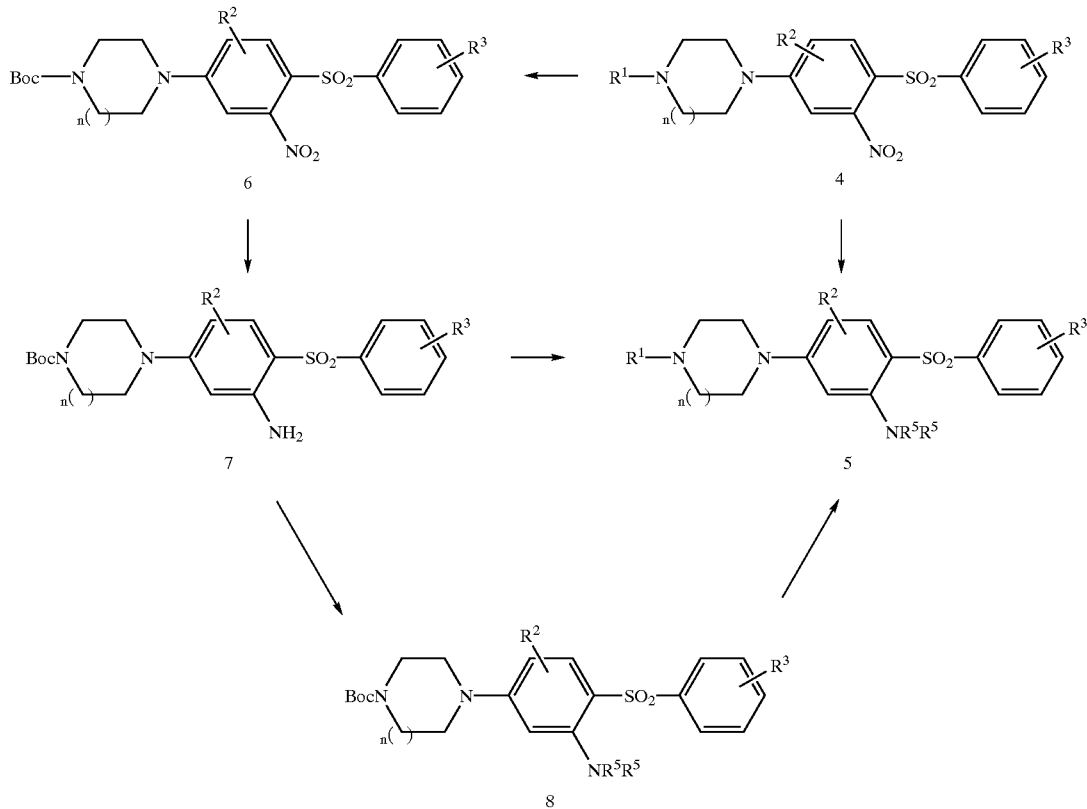
CHART II
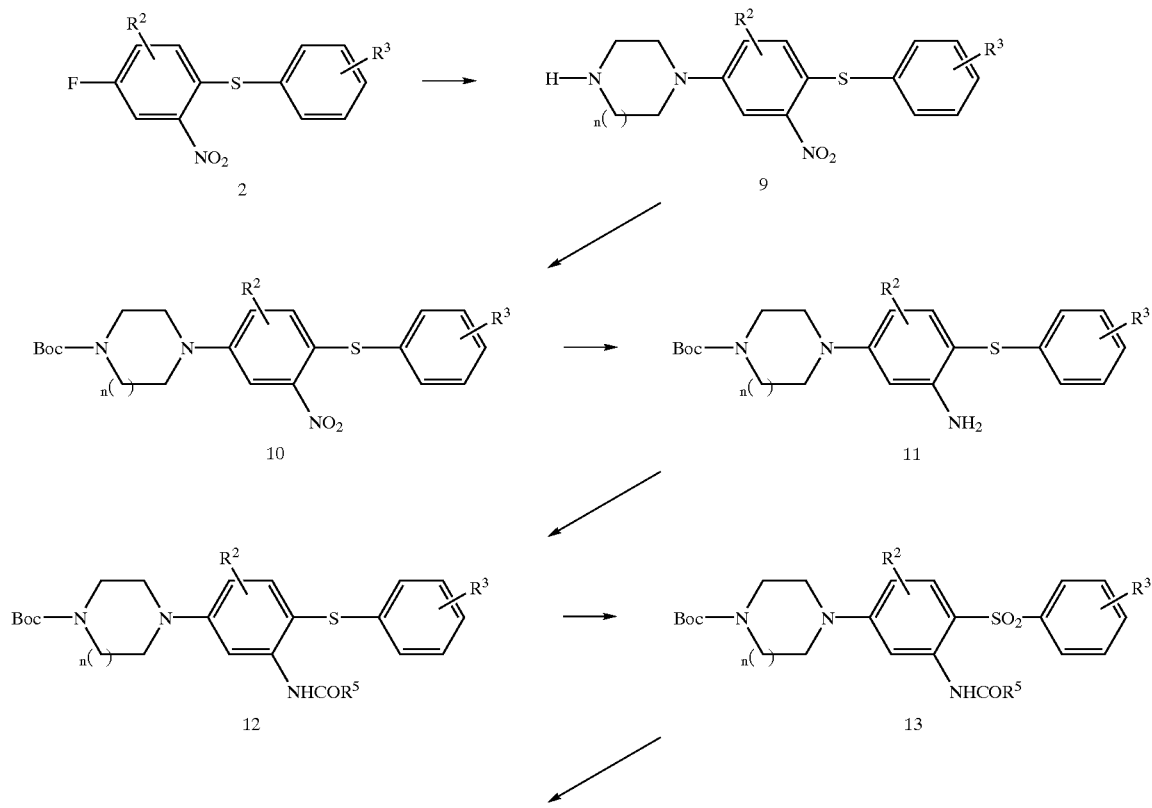

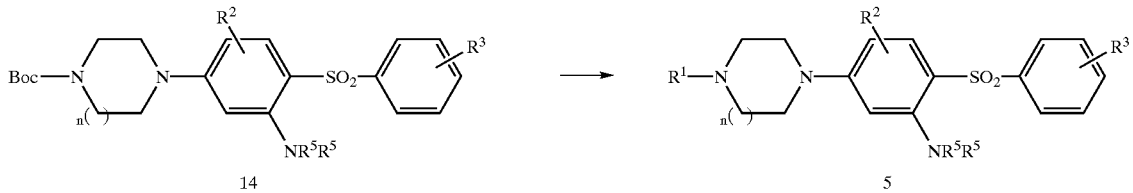

The invention also includes isotopically-labeled compounds, which are identical to those recited in Formulae I, II, and III, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{13}N$, $^{15}O$, $^{18}F$, $^{99m}Tc$, $^{123}I$, and $^{125}I$. Compounds of the present invention and pharmaceutically acceptable salts and prodrugs of said compounds that contain the aforementioned isotopes and/or other isotopes of other atoms are within the scope of the invention. Isotopically-labeled compounds of the present invention are useful in drug and/or substrate tissue distribution and target occupancy assays. For example, isotopically labeled compounds are particularly useful in SPECT (single photon emission computed tomography) and in PET (positron emission tomography).

Single-photon emission computed tomography (SPECT), acquires information on the concentration of isotopically labeled compounds introduced to a mammal's body. SPECT dates from the early 1960's, when the idea of emission traverse section tomography was introduced by D. E. Kuhl and R. Q. Edwards prior to either PET, x-ray CT, or MRI. In general, SPECT requires isotopes that decay by electron capture and/or gamma emission. Example of viable SPECT isotopes include, but are not limited to, 123-iodine ($^{123}I$) and 99m-technetium ($^{99m}Tc$). Subjects are injected with a radioactively labeled agent, typically at tracer doses. The nuclear decay resulting in the emission of a single gamma ray which passes through the tissue and is measured externally with a SPECT camera. The uptake of radioactivity reconstructed by computers as a tomogram shows tissue distribution in cross-sectional images.

Positron emission tomography (PET) is a technique for measuring the concentrations of positron-emitting isotopes within the tissues. Like SPECT, these measurements are, typically, made using PET cameras outside of the living subjects. PET can be broken down into several steps including, but not limited to, synthesizing a compound to include a positron-emitting isotope; administering the isotopically labeled compound to a mammal; and imaging the distribution of the positron activity as a function of time by emission tomography. PET is described, for example, by Alavi et al. in Positron Emission Tomography. published by Alan R. Liss, Inc. in 1985.

Positron-emitting isotopes used in PET include, but are not limited to, Carbon-11, Nitrogen-13, Oxygen-15, and Fluorine-18. In general, positron-emitting isotopes should have short half-lives to help minimize the long term radiation exposure that a patient receives from high dosages required during PET imaging.

In certain instances, PET imaging can be used to measure the binding kinetics of compounds of this invention with 5-HT$_6$ serotonin receptors. For example, administering an isotopically labeled compound of the invention that penetrates into the body and binds to a 5-HT$_6$ serotonin receptor creates a baseline PET signal which can be monitored while administering a second, different, non-isotopically labeled compound. The baseline PET signal will decrease as the non-isotopically labeled compound competes for the binding to the 5-HT$_6$ serotonin receptor.

In general, compounds of formula I that are useful in performing PET or SPECT are those which penetrate the blood-brain barrier, exhibit high selectivity and modest affinity to 5-HT$_6$ serotonin receptors, and are eventually metabolized. Compounds that are non-selective or those that exhibit excessive or small affinity for 5-HT$_6$ serotonin receptors are, generally, not useful in studying brain receptor binding kinetics with respect to 5-HT$_6$ serotonin receptors. Compounds that are not metabolized may harm the patient. Preferred compounds for isotopic labeling and use in performing PET or SPECT include 5-(1,4-diazepan-1-yl)-2-[(3-fluorophenyl) sulfonyl]phenylamine; 5-(1,4-diazepan-1-yl)-N-ethyl-2-[(3-fluorophenyl) sulfonyl]aniline; N-[5-(1,4-diazepan-1-yl)-2-[(3-fluorophenyl)sulfonyl]phenyl] acetamide; N-[5-(1,4-diazepan-1-yl)-2-[phenylsulfonyl] phenyl]acetamide; and pharmaceutically acceptable salts thereof.

In other embodiments, nuclear magnetic resonance spectroscopy (MRS) imaging can be used to detect the overall concentration of a compound or fragment thereof containing nuclei with a specific spin. In general, the isotopes useful in NMR imaging include, but are not limited to, hydrogen-1, carbon-13, phosphorus-31, and fluorine-19. For instance, the compounds 5-(1,4-diazepan-1-yl)-2-[(3-fluorophenyl) sulfonyl]phenylamine; 5-(1,4-diazepan-1-yl)-N-ethyl-2-[(3-fluorophenyl) sulfonyl]aniline; N-[5-(1,4-diazepan-1-yl)-2-[(3-fluorophenyl)sulfonyl]phenyl]acetamide; and pharmaceutically acceptable salts thereof, when containing $^{19}F$, are useful in conducting NMR imaging.

Further, substitution with heavier isotopes such as deuterium, i.e., $^2H$, can afford certain therapeutic advantages resulting from greater metabolic stability, for example increased in vivo half-life or reduced dosage requirements and, hence, maybe preferred in some circumstances. Isotopically labeled compounds of Formula I of this invention can generally be prepared by carrying out the synthetic procedures described above by substituting an isotopically labeled reagent for a non-isotopically labeled reagent.

The inventive compounds may be used in their native form or as salts. In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, etoglutarate, and glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient, the composition being useful in combating CNS diseases. Pharmaceutical compositions containing a compound appropriate for CNS diseases' use are prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally (for example, by intravenous, intraperitoneal or intramuscular injection), topically (including but not limited to surface treatment, transdermal application, and nasal application), intravaginally, orally, or rectally, depending on whether the preparation is used to treat a specific disease.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices such as the osmotic release type devices developed by the Alza Corporation under the OROS trademark.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing 1 to 1000 mg, conveniently 5 to 750 mg, most conveniently, 5 to 400 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compositions can be administered orally or parenterally at dose levels, calculated as the free base, of about 0.01 to 300 mg/kg mammal body weight, preferably 0.1 to 50 mg/kg of mammal body weight, more preferably 1.0 to 30 mg/kg of mammal body weight, and can be used in man in a unit dosage form, administered one to four times daily in the amount of 1 to 1000 mg per unit dose.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The exact regimen for administration of the compounds and compositions disclosed herein will necessarily be dependent upon the needs of the individual subject being treated, the type of treatment and, of course, the judgment of the attending practitioner. The compounds of the present invention can be administered to an animal in need of treatment. In most instances, this will be a human being, but the treatment of livestock and companion animals is also specifically contemplated as falling within the scope of the instant invention.

Generally, compounds of the invention are 5-HT ligands. The ability of a compound of the invention to bind or act at a 5-HT receptor, or to bind or act selectively at a specific 5-HT receptor subtype can be determined using in vitro and in vivo assays that are known in the art. As used herein, the term "bind selectively" means a compound binds at least 2 times, preferably at least 10 times, and more preferably at least 50 times more readily to a given 5-HT subtype than to one or more other subtypes. Preferred compounds of the invention bind selectively to one or more 5-HT receptor subtypes.

The ability of a compound of the invention to act as a 5-HT receptor agonist or antagonist can also be determined using in vitro and in vivo assays that are known in the art. All of the Example compounds provided above are 5-HT ligands, with the ability to displace >50% of a radiolabeled test ligand from one or more 5-HT receptor subtypes at a concentration of 1 μM. The procedures used for testing such displacement are well known and illustrated below.

5-HT$_6$ Receport Binding Assay

Growth of Cells and Membrane Preparation

Hela cells containing the cloned human 5-HT$_6$ receptor are acquired from Dr. David R. Sibley's laboratory in National Institute of Health (see Sibley, D. R., *J. Neurochemistry*, 66, 47–56, 1996). Cells are grown in high glucose Dulbecco's modified Eagle's medium, supplemented with L-glutamine, 0.5% sodium pyruvate, 0.3% penicillin-streptomycin, 0.025% G-418 and 5% Gibco fetal bovine serum and then are harvested, when confluent, in cold phosphate buffered saline.

Harvested intact cells are washed once in cold phosphate-buffered saline. The cells are pelleted and resuspended in 100 ml of cold 50 mM Tris, 5 mM EDTA and 5 mM EGTA, pH 7.4. Homogenization is with a Vir Tishear generator, 4 cycles for 30 seconds each at setting 50. The homogenized cells are centrifuged at 700 RPM (1000×g) for 10 minutes and the supernatant is removed. The pellet is resuspended in 100 ml of the above buffer and rehomogenized for 2 cycles. The rehomogenized cells are then centrifuged at 700 RPM (1000×g) for 10 minutes and the supernatant is removed. The combined supernatant (200 ml) is centrifuged at 23,000 RPM (80,000×g) for 1 hour in a Beckman Rotor (42.1 Ti). The membrane pellet is resupended in 50–8-ml of assay buffer containing HEPES 20 mM, MgCl2 10 mM, NaCl 150 mM, EDTA 1 mM, pH 7.4 and stored frozen in aliqouts at −70° C.

5-HT$_6$ Receptor Binding Assay

The radioligand binding assay used [$^3$H]-lysergic acid diethylamide (LSD). The assay is carried out in Wallac 96-well sample plates by the addition of 11 μl of the test sample at the appropriate dilution (the assay employed 11 serial concentrations of samples run in duplicate), 11 μl of radioligand, and 178 μl of a washed mixture of WGA-coated SPA beads and membranes in binding buffer. The plates are shaken for about 5 minutes and then incubated at room temperature for 1 hour. The plates are then loaded into counting cassettes and counted in a Wallac MicroBeta Trilux scintillation counter.

Binding Constant (Ki) Determination

Eleven serial dilutions of test compounds are distributed to assay plates using the PE/Cetus Pro/Pette pipetter. These dilutions were, followed by radioligand and the bead-membrane mixture prepared as described above. The specifically bound cpm obtained are fit to a one-site binding model using GraphPad Prism ver. 2.0. Estimated IC$_{50}$ values are converted to Ki values using the Cheng-Prusoff equation (Cheng, Y. C. et al., *Biochem. Pharmacol.*, 22, 3099–108, 1973). The Ki values obtained from the assay are shown in Table 1.

TABLE 1

5-HT$_6$ receptor Binding Assay Data

| EXAMPLE NO. | Ki (nM) |
| --- | --- |
| 1 | 2.6 |
| 2 | 4.9 |
| 3 | 31 |
| 4 | 32 |
| 5 | 23 |
| 6 | 68 |
| 7 | 3.6 |
| 8 | 5.2 |
| 9 | 79 |
| 10 | 11 |
| 11 | 11 |
| 12 | 1.4 |
| 13 | 2.7 |
| 14 | — |

The compounds and their preparations of the present invention will be better understood in connection with the following examples, which are intended as an illustration of and not a limitation upon the scope of the invention.

EXAMPLE 1

Preparation of 2-(phenylsulfonyl)-5-(1-piperazinyl) phenylamine

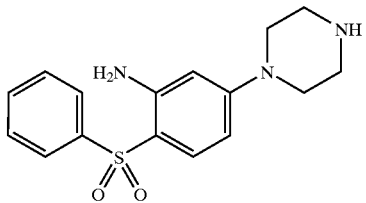

Step 1: Preparation of 4-fluoro-2-nitro-1-(phenylsulfanyl) Benzene

To a mixture of thiophenol (0.96 mL, 9.3 mmol) and potassium carbonate (1.4 g, 10.1 mmol) in 16 mL of dry acetonitrile is added 2,5-difluoronitrobenzene (1.0 mL, 9.2 mmol). The mixture is allowed to stir overnight at rt. Water (30 mL) and $CH_2Cl_2$ are added and the layers seperated. The aqueous layer is extracted with $CH_2Cl_2$ (3×25 mL). The combined organics are dried over $MgSO_4$, filtered, and concentrated. Recrystallization from EtOAc/heptane gives 2.3 g (99%) of the title compound as a solid, mp 66 67° C.

IR (drift) 1576, 1526, 1468, 1344, 1286, 1269, 1209, 946, 866, 819, 806, 756, 749, 693, 645 $cm^{-1}$; $^1H$ NMR (300 MHz, $CDCl_3$) δ 7.95, 7.54–7.60, 7.46–7.52, 7.07–7.15, 6.85; MS (EI) m/z 249 ($M^+$), 203, 202, 186, 185, 184, 78, 77.

Step 2: Preparation of 4-fluoro-2-nitro-1-(phenylsulfonyl) Benzene

A solution of 3-chloroperoxybenzoic acid (15 g, 87 mmol) in 110 mL of $CH_2Cl_2$ is slowly added to a mixture of 4-fluoro-2-nitro-1-(phenylsulfanyl) benzene (8.7 g, 35 mmol) and sodium bicarbonate (7.3 g, 87 mmol) in 260 mL of $CH_2Cl_2$, at −78° C. The solution is stirred at −78° C. for 1 h, then warmed to rt and allowed to stir overnight. The mixture is partitioned between $NaHCO_3$ (200 mL) and $CH_2Cl_2$ (3×100 mL). The combined organics are dried over $MgSO_4$, filtered and concentrated to a white solid. Recrystallization from EtOAc/heptane gives 9.7 g (99%) of the title compound as a solid, mp 127–129° C.;

IR (drift) 1602, 1590, 1551, 1371, 1329, 1318, 1274, 1227, 1161, 1083, 881, 811, 752, 728, 685 $cm^{-1}$; $^1H$ NMR (300 MHz, $CDCl_3$) δ 8.37–8.43, 7.92–8.00, 7.43–7.70; MS (EI) m/z 281 ($M^+$), 200, 188, 186, 170, 97, 93, 77.

Step 3: Preparation of 1-[3-nitro-4-(phenylsulfonyl) Phenyl] piperazine

A solution of 4-fluoro-2-nitro-1-(phenylsulfonyl) benzene (1.0 g, 3.6 mmol), piperazine (0.37 g, 4.3 mmol), and potassium carbonate (0.79 g, 5.7 mmol) is stirred in 35 mL of acetonitrile overnight at reflux. The mixture is cooled to rt and 35 mL of water and $CH_2Cl_2$ are added. The layers are separated and the aqueous layer extracted with $CH_2Cl_2$ (3×35 mL). The combined organics are dried over $MgSO_4$, filtered, and concentrated. Purification via flash column chromatography (15% MeOH/$CH_2Cl_2$) gives 1.1 g (92%) of title compound as a solid, mp 180–182° C.

IR (drift) 1601, 1536, 1448, 1367, 1358, 1303, 1254, 1153, 1138, 1085, 1022, 774, 750, 724, 688 $cm^{-1}$; $^1H$ NMR (300 MHz, $CDCl_3$) δ 8.10, 7.89–7.95, 7.47–7.55, 6.95–7.05, 3.31–3.45, 2.96–3.08, 2.51; MS (EI) m/z 347 ($M^+$), 305, 275, 258, 152, 118, 77.

Step 4: Preparation of Tert-Butyl 4-[3-nitro-4-(phenylsulfonyl)phenyl]-1-piperazinecarboxylate To a solution of 1-[3-nitro-4-(phenylsulfonyl) phenyl] piperazine (1.5 g, 4.3 mmol) and NaOH (0.38 g, 9.5 mmol) in 64 mL of a 1:1 $THF:H_2O$ solvent system is added a solution of di-tert-butyl dicarbonate (1.0 g, 4.7 mmol) in 5 mL of THF. The solution is stirred at rt for 16 h. The mixture is neutralized with 6 N HCl and 25 mL of EtOAc is added. The layers are separated and the aqueous layer is extracted with EtOAc (3×25 mL). The combined organics are dried over $MgSO_4$, filtered, and concentrated. Recrystallization from EtOAc/hexane gives 1.7 g (87%) of the title compound as solid, mp 190–191° C.

IR (drift) 1690, 1607, 1544, 1415, 1362, 1350, 1322, 1306, 1290, 1243, 1177, 1151, 1138, 748, 688 $cm^{-1}$; $^1H$ NMR (300 MHz, $CDCl_3$) δ 8.13, 7.89–7.97, 7.47–7.62, 6.96–7.05, 3.53–3.64, 3.34–3.45, 1.48; MS (EI) m/z 447 ($M^+$), 305, 275, 258, 152, 91, 77.

Step 5: Preparation of Tert-Butyl 4-[3-amino-4-(phenylsulfonyl)phenyl]-1-piperazinecarboxylate To a solution of tert-butyl 4-[3-nitro-4-(phenylsulfonyl) phenyl]-1-piperazinecarboxylate (0.85 g, 1.8 mmol) in 20 mL of a 4:1 EtOH:THF solvent system is added Raney nickel (130 mg suspension in EtOH) followed by hydrazine monohydrate (0.44 mL, 9.1 mmol). The mixture is stired vigorously for 2 h and then filtered through celite that is pretreated with water. The filtrate is concentrated, and the residue crystallized from MeOH/EtOAc/hexane to give 0.76 g (99%) of the aniline as a white solid, mp 135–137° C.

IR (drift) 1693, 1602, 1552, 1448, 1420, 1390, 1366, 1306, 1288, 1249, 1224, 1168, 1142, 1097, 736 $cm^{-1}$; $^1H$ NMR (300 MHz, $CDCl_3$) δ 7.85–7.93, 7.68, 7.41–7.56, 6.32, 5.98, 5.09, 3.48–3.58, 3.18–3.28, 1.47; MS (EI) m/z 417 ($M^+$), 361, 317, 275, 167, 91, 77

Step 6: Preparation of 2-(phenylsulfonyl)-5-(1-piperazinyl) phenylamine

To a solution of tert-butyl 4-[3-amino-4-(phenylsulfonyl) phenyl]-1-piperazinecarboxylate (0.68 g, 1.6 mmol) in 18 mL of $CH_2Cl_2$ at 0° C., is added trifluoroacetic acid (18 mL). The solution is stirred at 0° C. for 2 h and then concentrated. Methylene chloride (30 mL) and 1 N NaOH (30 mL) are added and the layers seperated. The aqueous layer is extracted with $CH_2Cl_2$ (3×25 mL) and the combined organic layers dried over $MgSO_4$, filtered, and concentrated to give 0.46 g (89%) of a white solid. The solid is dissolved in 50 mL of MeOH and HCl/MeOH (5 mL) is added slowly and stirred under $N_2$ for 2 min. The solvent is removed under vacuum to give a white solid. Recrystallization from MeOH/EtOAc/hexane gives the pure title compound as the hydrogen chloride salt, mp 165–166° C.

IR (drift) 3371, 2831, 1600, 1550, 1447, 1304, 1284, 1260, 1225, 1140, 1092, 1034, 736, 688, 602 $cm^{-1}$; $^1H$ NMR (300 MHz, $CDCl_3$) δ 7.86–7.94, 7.66, 7.40–7.55, 6.33, 5.98, 5.03, 3.16–3.30, 2.91–3.04, 2.31; MS (EI) m/z 317 ($M^-$), 276, 275, 91, 77.

EXAMPLE 2

Preparation of 5-(1,4-diazepan-1-yl)-2-[(3-fluorophenyl) sulfonyl]phenylamine

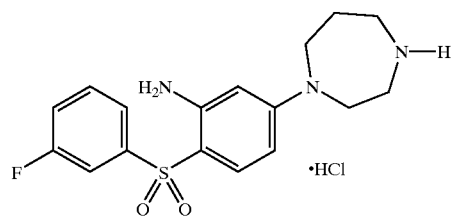

A solution of 1-[4-[(3-fluorophenyl)sulfonyl]-3-nitrophenyl]-1,4-diazepane (using the similar procedure as described in EXAMPLE 1, step 3, 0.382 g, 1.10 mmol) and Pd/C (0.0573 g, 15% by wt. of IV) in 35 mL of a 4:1 EtOH:THF solvent is exposed to hydrogen gas (25 psi) in a Parr bottle. The pressure of hydrogen is constantly monitored and kept near 25 psi. After 2 h, the mixture is filtered, the solids rinsed with MeOH and $CH_2Cl_2$, and the filtrate concentrated to give 0.349 g (99%) of a while solid. The HCl salt is prepared by standard methods to give an off-white solid. Recrystallization from hot MeOH/EtOAc/hexane gives a nearly quantitative yield of the title compound as hydrochloride salt, mp 106–108° C.

IR (drift) 1600, 1550, 1506, 1474, 1458, 1313, 1290, 1270, 1222, 1135, 1085, 727, 691, 678, 651 cm$^{-1}$; $^1$H NMR (300 MHz, CDCl$_3$) δ 7.67–7.71, 7.56–7.63, 7.35–7.47, 7.10–7.23, 6.17, 5.80, 4.95, 3.48–3.59, 3.00, 2.83, 2.11, 1.81–1.92; MS (EI) m/z 349 (M$^+$), 307, 293, 281, 148.

EXAMPLE 3

Preparation of 2-[(4-fluorophenyl)sulfonyl]-5-(1-piperazinyl) Phenylamine

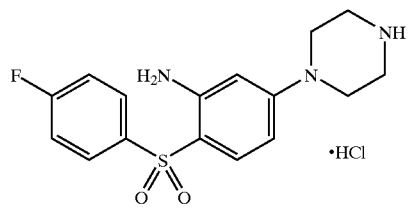

Following the general procedure of EXAMPLE 2 and making non critical variations, 2,5-difluoronitrobenzene is converted to the title compound, mp144–146

IR (drift) 2924, 2919, 2685, 2676, 2589, 1599, 1552, 1492, 1451, 1286, 1265, 1236, 1141, 1092, 601 cm$^{-1}$; $^1$H NMR (300 MHz, CDCl$_3$) δ 7.83–7.91, 7.64, 7.03–7.12, 6.69–6.74, 6.23–6.30, 3.46, 3.06–3.15, 2.81–2.89; MS (EI) m/z 335 (M$^+$), 293, 96, 95, 93, 91, 83

EXAMPLE 4

Preparation of 2-[(4-fluorophenyl)sulfonyl]-5-(4-methyl-1-piperazinyl) Phenylamine

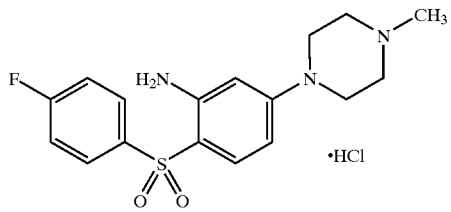

Following the general procedure of EXAMPLE 2 and making non critical variations, the title compound is obtained, mp 85–89° C.

IR (drift) 2957, 2926, 2850, 2828, 2793, 2714, 1592, 1552, 1492, 1450, 1287, 1238, 1139, 1090, 837 cm$^{-1}$; $^1$H NMR (300 MHz, MeOH-d$_4$) δ 8.30, 7.64–7.75, 7.37, 7.04–7.12, 3.36–3.44, 2.54–2.62, 2.36, 1.67; MS (EI) m/z 349 (M$^+$), 334, 279, 213, 120, 96, 91.

EXAMPLE 5

Preparation of 2-[(4-methylphenyl)sulfonyl]-5-(1-piperazinyl) Phenylamine

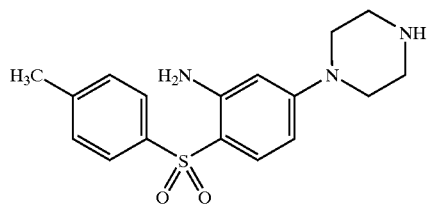

Following the general procedure of EXAMPLE 1 (Steps 1–6) and making non critical variations, the title compound is obtained, mp 102–106° C.

IR (drift) 1599, 1551, 1448, 1302, 1282, 1262, 1139, 1092, 812, 728, 705, 680, 671, 667, 657 cm$^{-1}$; $^1$H NMR (300 MHz, CDCl$_3$) δ 7.77, 7.66, 7.20–7.30, 6.31, 5.97, 5.09, 3.17–3.30, 2.93–3.03, 2.37; MS (EI) m/z 331 (M$^+$), 290, 289, 119, 93, 92, 91, 65, 57, 56.

EXAMPLE 6

Preparation of 2-[(4-methylphenyl)sulfonyl]-5-(4-methyl-1-piperazinyl) Phenylamine

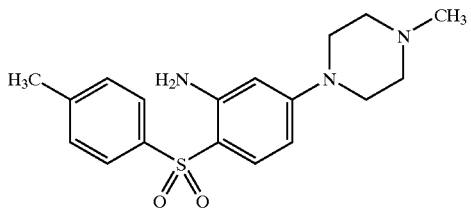

Following the general procedure of EXAMPLE 1 (Steps 1–6) and making non critical variations, the title compound is obtained, mp 148–151° C.

IR (drift) 3334, 2954, 2857, 1598, 1552, 1453, 1296, 1288, 1255, 1140, 1095, 833, 759, 708, 654 cm$^{-1}$; $^1$H NMR (300 MHz, CDCl$_3$) δ 8.42–8.60, 7.72–7.81, 7.62–7.72, 7.20–7.33, 6.58, 6.20–6.30, 6.00, 5.12, 3.35–3.50, 2.83, 2.60, 2.38; MS (EI) m/z 345 (M$^+$), 330, 120, 92, 91, 71, 65, 58, 57, 56.

EXAMPLE 7

Preparation of 5-(4-methyl-1-piperazinyl)-2-(phenylsulfonyl) Phenylamine

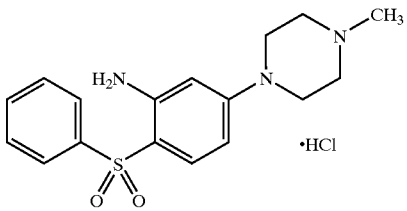

Following the general procedure of EXAMPLE 2 and making non critical variations, the title compound is obtained, mp 90–93° C.

IR (drift) 3458, 3370, 2843, 1601, 1552, 1448, 1289, 1264, 1230, 1140, 1095, 737, 689, 644, 610cm$^{-1}$; $^1$H NMR (300 MHz, CDCl$_3$) δ 7.87–7.92, 7.71, 7.66, 7.42–7.51, 6.75, 6.33, 5.98, 5.03, 3.27–3.33, 3.25–3.29, 2.56–2.59, 2.48–2.52, 2.36, 2.33; MS (EI) m/z 331 (M$^+$), 316, 261, 92, 78.

EXAMPLE 8

Preparation of 2-[(3-fluorophenyl)sulfonyl]-5-(4-methyl-1-piperazinyl) Phenylamine

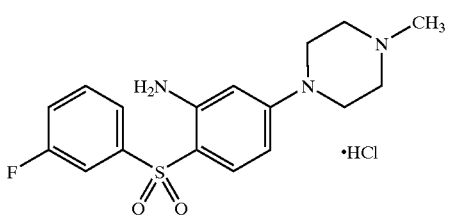

Following the general procedure of EXAMPLE 2 and making non critical variations, the title compound is obtained, mp 89–92° C.

IR (drift) 2670, 2580, 2467, 2446, 1601, 1552, 1474, 1451, 1293, 1267, 1222, 1135, 1087, 697, 616 cm$^{-1}$; $^1$H NMR (300 MHz, CDCl$_3$) δ 7.30, 7.11–7.19, 6.82–6.86, 6.68–6.78, 6.38, 6.31, 4.24, 3.20–3.28, 2.55–2.59, 2.36; MS (EI) m/z 349 (M$^+$), 334, 279, 91, 86.

EXAMPLE 9

Preparation of 5-(1,4-diazepan-1-yl)-2-[(3,4-difluorophenyl)sulfonyl]phenylamine

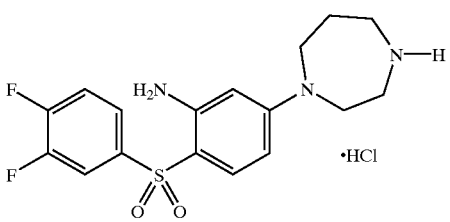

Following the general procedure of EXAMPLE 2 and making non-critical variations, the title compound is obtained.

MS (EI) m/z 367 (M+), 311, 299, 134, 122, 119, 91, 70, 65, 63, 57.

EXAMPLE 10

Preparation of 5-(1,4-diazepan-1-yl)-2-(phenylsulfonyl) Phenylamine

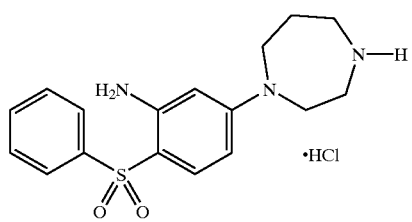

Following the general procedure of EXAMPLE 2 and making non critical variations but using 1-[4-[(phenyl)sulfonyl]-3-nitrophenyl]-1,4-diazepane as a starting material, the title compound is obtained. MS (FAB) m/z 332 (MH+), 486, 408, 348, 334, 333, 332, 331, 330, 191, 44.

EXAMPLE 11

Preparation of 5-(1,4-diazepan-1-yl)-2-[(3,5-difluorophenyl)sulfonyl]phenylamine

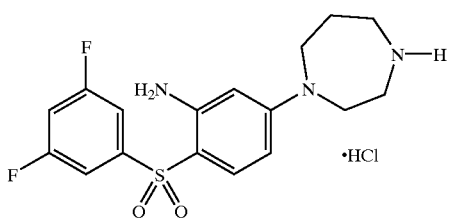

Following the general procedure of EXAMPLE 2 and making non critical variations, the title compound is obtained.

MS (EI) m/z 367 (M+), 325, 311, 299, 146, 119, 113, 91, 84, 69, 57.

EXAMPLE 12

Preparation of 5-(1,4-diazepan-1-yl)-2-[(3-fluorophenyl) sulfonyl]-N-methylphenylamine

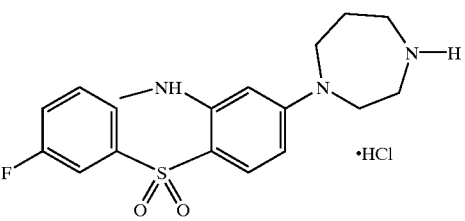

tert-Butyl 4-[3-amino-4-(phenylsulfonyl)phenyl]-5-(1,4-diazepan-1-yl)-1-carboxylate (prepared as described in EXAMPLE 1, step 5; 2.3 g, 5.1 mmol) and methyl trifluoromethane sulfonate (0.58 mL, 5.1 mmol) in 54 mL of dry THF is added sodium hydride (0.21 g, 5.1 mmol) in small portions. Upon complete addition, the mixture is stirred overnight under a blanket of N$_2$. The solution is quenched by the addition of 55 mL of NH$_4$Cl and the layers are separated. The aqueous layer is extracted with EtOAc (3×50 mL). The combined organic layers are dried over MgSO$_4$, filtered, and concentrated. Purification via column chromatography (30% EtOAc/hexane) gives the desired methylaniline. The carbamate is deprotected following the synthetic route for EXAMPLE 1 (step 6) to give 0.11 g (6.0% overall) of the title compound as a solid. Recrystallization from MeOH/EtOAc/hexane gives the pure product as the HCl salt, mp 153–154° C.

IR (drift) 2944, 2811, 2734, 2685, 1596, 1560, 1468, 1290, 1270, 1220, 1133, 795, 732, 691, 677 cm$^{-1}$; $^1$H NMR (300 MHz, CDCl$_3$) δ 7.45–7.65, 7.34–7.45, 7.12–7.21, 6.15–6.30, 6.10, 5.72, 3.51–3.60, 3.30–3.44, 3.01, 2.81, 2.27, 1.80–1.91; MS (EI ) m/z 363 (M$^+$), 307, 295, 234, 216, 146, 81, 77.

EXAMPLE 13

Preparation of N-ethyl-2-(phenylsulfonyl)-5-(1-piperazinyl) Phenylamine

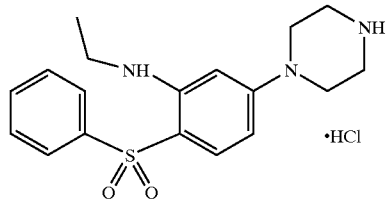

·HCl

Step 1: Preparation of 1-[3-nitro-4-(phenylsulfanyl)phenyl]piperazine

To a mixture of piperazine (1.0 g, 12 mmol) and potassium carbonate (2.0 g, 14 mmol) in 80 mL of dry acetonitrile is added 4-fluoro-2-nitro-1-(phenylsulfanyl) benzene (2, EXAMPLE 1, step 1, 2.7 g, 9.5 mmol). The mixture is allowed to stir overnight at rt. Water and $CH_2Cl_2$ (80 mL each) are added and the layers separated. The aqueous layer is extracted with $CH_2Cl_2$ (3×50 mL). The combined organic layers are dried over $MgSO_4$, filtered, and concentrated. Purification via column chromatography (50% EtOAc/hexane) gives 1.6 g (47%) of the title compound as a red oil.

IR (drift) 3683, 3020, 2400, 1547, 1521, 1441, 1338, 1295, 1215, 851, 758, 754, 707, 692, 669 cm$^{-1}$; $^1$H NMR (300 MHz, CDCl$_3$) δ 7.63, 7.35–7.60, 6.90–7.00, 6.81–6.96, 3.16–3.23, 3.02–3.08; MS (EI) m/z 315 (M$^+$), 273, 243, 226, 184, 139, 84, 77.

Step 2: Preparation of tert-butyl 4-[3-nitro-4-(phenylsulfanyl)phenyl]-1-piperazinecarboxylate To a solution of 1-[3-nitro-4-(phenylsulfanyl)phenyl]piperazine (1.6 g, 4.5 mmol) and NaOH (0.39 g, 9.8 mmol) in 64 mL of a 1:1 THF:H$_2$O solvent system is added a solution of di-tert-butyl dicarbonate (1.1 g, 4.9 mmol) in 5 mL of THF. The solution is stirred at rt for 16 h. The mixture is made neutral with 6 N HCl and 25 mL of EtOAc is added. The layers are separated and the aqueous layer is extracted with EtOAc (3×25 mL). The combined organic layers are dried over MgSO$_4$, filtered, and concentrated. Purification by column chromatography (15% EtOAc/hexane) gives 1.7 g (85%) of the title compound as a oil.

IR (drift) 3437, 3344, 2976, 1682, 1613, 1595, 1501, 1429, 1365, 1290, 1258, 1221, 1165, 1128, 733 cm$^{-1}$; $^1$H NMR (300 MHz, CDCl$_3$) δ 7.66, 7.49–7.57, 7.39–7.47, 6.98, 6.85, 3.56–3.64, 3.13–3.23, 1.50; MS (EI) m/z 415 (M$^+$), 385, 329, 285, 244, 243, 227, 151.

Step 3: Prepartion of Tert-Butyl 4-[3-amino-4-(phenylsulfanyl)phenyl]-1-piperazinecarboxylate To a solution of tert-butyl 4-[3-nitro-4-(phenylsulfanyl)phenyl]-1-piperazinecarboxylate (1.7 g, 3.8 mmol) in 42 mL of a 4:1 EtOH:THF solvent system is added Raney nickel (260 mg suspension in EtOH) followed by hydrazine monohydrate (0.92 mL, 19 mmol). The mixture is stirred vigorously for 2 h and then filtered through celite that is pretreated with water. The filtrate is concentrated, the residue crystallized from MeOH/EtOAc/hexane to give 1.5 g (92%) of the aniline as a white foam.

IR (drift) 3344, 2976, 1682, 1613, 1595, 1501, 1430, 1365, 1290, 1259, 1221, 1166, 766, 733, 687 cm$^{-1}$; $^1$H NMR (300 MHz, CDCl$_3$) δ 7.34, 7.16–7.24, 7.02–7.11, 6.30–6.41, 4.34, 3.54–3.64, 3.15–3.24, 1.49; MS (EI) m/z 385 (MH+), 285, 244, 243, 229, 227, 151, 104.

Step 4: Preparation of Tert-Butyl 4-[3-(acetylamino)-4-(phenylsulfanyl)phenyl]-1-piperazinecarboxylate A solution of tert-butyl 4-[3-amino-4-(phenylsulfanyl)phenyl]-1-piperazinecarboxylate (0.69 g, 1.6 mmol) in 7 mL of dry CH$_2$Cl$_2$ is cooled to 0° C. Acetyl chloride (0.13 mL, 1.8 mmol), diisopropylethylamine (0.32 mL, 1.8 mmol), and DMAP (0.020 g, 0.16 mmol) are added and the solution allowed to warm to rt overnight with stirring. Water and CH$_2$Cl$_2$ (10 mL each) are added and the layers separated. The aqueous layer is extracted with CH$_2$Cl$_2$ (3×10 mL) and the combined organic layers are washed with 1 N HCl, H$_2$O, and brine. After drying over MgSO$_4$, the mixture is filtered and concentrated to give the crude product. Purification by column chromatography (25% EtOAc/hexane) gives 0.70 g (99%) of the titel compound as a oil.

IR (mull) 1694, 1596, 1582, 1557, 1518, 1440, 1430, 1395, 1294, 1271, 1238, 1179, 1120, 744, 739 cm$^{-1}$; $^1$H NMR (300 MHz, CDCl$_3$) δ 8.22–8.26, 8.20, 7.46, 7.19–7.26, 7.10–7.15, 7.01–7.03, 6.68, 3.56–3.61, 3.25–3.29, 2.05, 1.48; MS (EI) m/z 427 (M$^+$), 371, 327, 285, 227, 218, 161, 147, 134.

Step 5: Preparation of Tert-Butyl 4-[3-(acetylamino)-4-(phenylsulfonyl)phenyl]-1-piperazinecarboxylate A mixture of 3-chloroperoxybenzoic acid (1.3 g, 7.7 mmol) in 17 mL of CH$_2$Cl$_2$ is added to a mixture of tert-butyl 4-[3-(acetylamino)-4-(phenylsulfanyl)phenyl]-1-piperazinecarboxylate (1.3 g, 3.1 mmol) and NaHCO$_3$ (0.65 g, 7.7 mmol) in 36 mL of CH$_2$Cl$_2$, cooled to –78° C. The solution is stirred at –78° C. for 1 h and then warmed to rt and stirred for 6 additional hours. The mixture is partitioned between NaHCO$_3$ (50 m/L) and CH$_2$Cl$_2$ (3×50 mL), dried over MgSO$_4$, filtered, and concentrated. Purification by column chromatography (10% MeOH/CH$_2$Cl$_2$) gives 0.51 g (36%) of the pure title compound as a solid, mp 129–130

IR (drift) 1697, 1592, 1461, 1442, 1418, 1393, 1366, 1287, 1264, 1252, 1174, 1149, 1036, 752, 690 cm$^{-1}$; $^1$H NMR (300 MHz, CDCl$_3$) δ 10.48, 8.70–8.75, 8.26, 7.70, 7.44–7.56, 3.84–4.24, 3.60–3.83, 3.41, 3.08–3.18, 2.11; MS (EI) m/z 459 (M$^+$), 310,261,218, 185, 161, 150, 128,85,77.

Step 6: Preparation of Tert-Butyl 4-[3-(ethylamino)-4-(phenylsulfonyl)phenyl]-1-piperazinecarboxylate To a mixture of tert-butyl 4-[3-(acetylamino)-4-(phenylsulfonyl)phenyl]-1-piperazinecarboxylate (0.44 g, 0.96 mmol) in 7 nL of dry THF is added borane-methyl sulfide complex (0.28 mL, 2.8 mmol, 10.0 M). The mixture is stirred at rt overnight. The reaction is quenched upon dropwise addition of 10% HCl. Water (3.0 mL) and KOH (2.0 g) are added, the mixture heated at reflux for 6 h. At that time methanol (2 mL) is added and the mixture stirred at reflux overnight. After cooling to rt, the organics are removed under reduced pressure, the aqueous layer is saturated with NaCl, and extracted with CH$_2$Cl$_2$ (3×10 mL). The combined organic layers are dried over MgSO$_4$, filtratered, and concentrated to give the crude product. Purification by column chromatography (15% EtOAc/hexane) gave 0.18 g (43%) of the pure title compound as an oil.

IR (drift) 2970, 1690, 1592, 1561, 1476, 1457, 1430, 1363, 1288, 1243, 1215, 1173, 1128, 993, 743 cm$^{-1}$; $^1$H NMR (300 MHz, CDCl$_3$) δ 7.48–7.55, 7.36–7.46, 7.32, 6.20, 5.96, 5.90, 3.49–3.59, 3.17–3.25, 2.82–3.06, 1.47, 1.05; MS (EI) m/z 445 (M+), 414, 357, 324, 280, 271, 147, 136, 104, 58, 57.

Step 7: Preparation of N-ethyl-2-(phenylsulfonyl)-5-(1-piperazinyl)phenylamine

To a solution of tert-butyl 4-[3-(ethylamino)-4-(phenylsulfonyl)phenyl]-1-piperazinecarboxylate (0.18 g, 0.40 mmol) in 4.6 mL of CH$_2$Cl$_2$ at 0° C. is added trifluoroacetic acid (4.6 mL). The solution is stirred at 0° C. for 2 h and then concentrated. Methylene chloride (10 mL) and 1 N NaOH (10 mL) are added and the layers seperated. The aqueous layer is extracted with $CH_2Cl_2$ (3×15 mL) and the combined organic layers are dried over $MgSO_4$, filtered, and concentrated to give 0.13 g (86%) of a white solid. The solid is dissolved in 25 mL of MeOH and HCl/MeOH (5 mL) is added slowly. The solvent is removed under vacuum to give a white solid. Recrystallization from MeOH/EtOAc/hexane gives the pure title compound as the hydrogen chloride salt, mp 121–123° C.

IR (drift) 2957, 2932, 2822, 2778, 2747, 2720, 2692, 1599, 1588, 1566, 1512, 1449, 1440, 1220, 739 $cm^{-1}$; $^1H$ NMR (300 MHz, $CDCl_3$) δ 7.36, 7.17–7.25, 7.03–7.12, 6.30, 6.20, 4.77–4.85, 3.22–3.29, 3.11–3.22, 3.03–3.10, 2.00, 1.18; MS (EI) m/z 345 ($M^+$), 313, 271, 147, 136, 133, 117, 91, 77.

EXAMPLE 14

Preparation of 5-(1,4-diazepan-1-yl)-N-ethyl-2-[(3-fluorophenyl) sulfonyl]aniline Hydrochloride

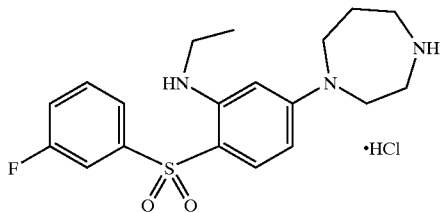

Following the general procedure of EXAMPLE 13 (Steps 1–7) and making non critical variations, 1-[4-fluoro-2-nitro-1-(phenylsulfanyl)]-3-fluorobenzene (prepared as described in EXAMPLE 1, step I) is converted to the title compound, MS (EI) m/z 377 (M+), 321, 310, 309, 135, 131, 119, 117, 83, 77, 69.

EXAMPLE 15

Preparation of N-[5-(1,4-diazepan-1-yl)-2-[(3-fluorophenyl)sulfonyl]phenyl]acetamide and its Methanesulfonate

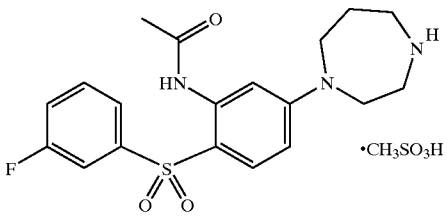

Step 1: Preparation of 4-fluoro-2-nitrophenyl 3-fluorophenyl Sulfide

To a mixture of 3-fluorothiophenol (8.36 g, 65.2 mmol) and potassium carbonate (9.81 g, 71.0 mmol) in 115 mL of dry acetonitrile is added 2,5-difluoronitrobenzene (7.00 mL, 64.55 mmol). The mixture is allowed to stir at room temperature for 2 hours. Water and $CH_2Cl_2$ (120 mL each) are added and the layers separated. The aqueous layer is extracted with $CH_2Cl_2$ (3×50 mL). The combined organics are dried over $MgSO_4$, filtered, and concentrated to give a bright yellow solid. The solid is triturated with hexane to give 17.1 g (99%) of the title compound as a bright yellow solid.

$^1H$ NMR (300 MHz, $CDCl_3$) δ 7.95, 7.41–7.51, 7.33–7.38, 7.26–7.31, 7.12–7.24, 6.91.

Step 2: Preparation of 4-fluoro-2-nitrophenyl 3-fluorophenyl Sulfone

A mixture of 4-fluoro-2-nitrophenyl 3-fluorophenyl sulfide (17.1 g, 64.1 mmol) in 430 mL of glacial acetic acid is heated to 100° C. and treated with 7.4 mL of a 30% $H_2O_2$ solution. After stirring for 20 min at 100° C., another 7.4 mL of the $H_2O_2$ solution is added and the mixture stirred at 100° C. for an additional 30 min. After cooling to room temperature, the mixture is diluted with 450 mL of water and the resulting white solid is filtered. The solids are rinsed with 1 N NaOH, and water until neutral to litmus, triturated with hexane, and dried under vacuum to give 18.5 g (96%) of the title compound as a white solid.

$^1H$ NMR (300 MHz, $CDCl_3$) δ 8.38–8.43, 7.74–7.77, 7.62–7.66, 7.47–7.60, 7.31–7.48.

Step 3: Preparation of 4-(1,4-diazepan-1-yl)-2-nitrophenyl 3-fluorophenyl Sulfone A mixture of 4-fluoro-2-nitrophenyl 3-fluorophenyl sulfone (5.00 g, 16.7 mmol), homopiperazine (2.09 g, 20.9 mmol), and potassium carbonate (3.46 g, 25.1 mmol) in 140 mL of dry acetonitrile is stirred vigorously for 4 h at 60° C. After cooling to room temperature, water and $CH_2Cl_2$ (140 mL each) are added and the layers separated. The aqueous layer extracted with $CH_2Cl_2$ (3×50 mL). The combined organics are dried over $MgSO_4$, filtered, and concentrated to give an orange solid. The crude product is triturated with a hot $Et_2O:CH_2Cl_2$ mixture (4:1 ) until solid. Further trituration with hot EtOAc/hexane gave 6.31 g (99%) of the title compound as bright yellow solid.

$^1H$ NMR (300 MHz, $CDCl_3$) δ 8.05, 7.71–7.76, 7.59–7.64, 7.46–7.54, 7.22–7.30, 6.90, 6.83, 3.54–3.70, 3.00–3.07, 2.80–2.88, 1.82–1.94.

Step 4: Preparation of Tert-Butyl 4-[4-[(3-fluorophenyl)sulfonyl]-3-nitrophenyl]-1,4-diazepane-1-carboxylate To a mixture of 4-(1,4-diazepan-1-yl)-2-nitrophenyl 3-fluorophenyl sulfone (49.1 g, 129 mmol) and sodium hydroxide (11.4 g, 286 mmol) in 650 ml of a 1:1 $THF:H_2O$ solvent is slowly added a mixture of di-tert-butyl dicarbonate (32.4 g, 148 mmol) in 5 ml of THF. The solution is stirred at rt for 16 h. The mixture is neutralized with 6 N HCl and 200 mL of $CH_2Cl_2$ is added. The layers are separated and the aqueous layer extracted with $CH_2Cl_2$ (3×100 mL). The combined organics are dried over $MgSO_4$, filtered, and concentrated to give an orange solid. The crude product is triturated with EtOAc and hexane to give 60.35 g (99%) of the title compound as a bright yellow solid.

$^1H$ NMR (400 MHz, $CDCl_3$) δ 8.12, 7.76–7.80, 7.63–7.67, 7.52–7.58, 7.31–7.34, 6.94–6.97, 6.87–6.92, 3.62–3.75, 3.39–3.45, 3.30–3.35, 1.94–2.03, 1.42, 1.34.

Step 5: Preparation of Tert-Butyl 4-[3-amino-4-[(3-fluorophenyl)sulfonyl]Phenyl]-1,4-diazepane-1-carboxylate A mixture of tert-butyl 4-{4-[(3-fluorophenyl)sulfonyl]-3-nitrophenyl}-1, 4-diazepane-1-carboxylate (58.0 g, 121 mmol) and Pd/C (8.70 g, 15% by wt.) in 1.5 L of a 2:2:1 THF:MeOH:EtOH solvent is exposed to hydrogen gas (25 psi) in a Parr bottle. The pressure of hydrogen is constantly monitored and kept near 25 psi. After 16 h, the mixture is filtered, solids rinsed with MeOH and $CH_2Cl_2$, and filtrate concentrated to give a brown solid. The solid is triturated with EtOAc and hexane to give 53.4 g (98%) of the title compound as an off white solid.

$^1H$ NMR (400 MHz, $CDCl_3$) δ 7.72–7.76, 7.64, 7.44–7.51, 7.21–7.27, 6.22–7.26, 5.84–5.87, 5.03–5.09, 3.52–3.63, 3.33–3.38, 3.23–3.29, 1.91–1.99, 1.45, 1.34.

Step 6: Preparation of Tert-Butyl 4-[3-(acetylamino)-4-[(3-fluorophenyl)sulfonyl]phenyl]-1,4-diazepane-1-carboxylate A mixture of tert-butyl 4-[3-amino-4-[(3-fluorophenyl)sulfonyl]phenyl]-1,4-diazepane-1-carboxylate (0.29 g, 0.66 mmol) and anhydrous acetic anhydride (1.0 mL) is stirred at 60° C. for 1 h under a nitrogen atmosphere. After cooling to rt, 5 mL of toluene is added and the mixture concentrated. The crude product is triturated with more toluene then with EtOAc and $Et_2O$ to give 0.31 g (97%) of the title compound as a white solid.

$^1$H NMR (400 MHz, $CDCl_3$) δ 9.50–9.66, 7.78–7.85, 7.67, 7.51–7.54, 7.37–7.45, 7.14–7.19, 6.35–6.44, 3.50–3.58, 3.21–3.27, 3.12–3.17, 2.15, 1.86–1.94, 1.33, 1.28.

Step 7: Preparation of N-[5-(1,4-diazepan-1-yl)-2-[(3-fluorophenyl)sulfonyl]Phenyl]acetamide Methanesulfonate To a mixture of tert-butyl 4-[3-(acetylamino)-4-[(3-fluorophenyl)sulfonyl]phenyl]-1,4-diazepane-1-carboxylate (0.508 g, 1.03 mmol) in 20 mL of a 1:1 $Et_2O:CH_2Cl_2$ solvent is added anhydrous methanesulfonic acid (0.109 g, 1.14 mmol) and the mixture is stirred at rt for 2.5 h. Hot $Et_2O$ (10 mL) is added and the white solid is filtered, rinsed with $Et_2O$ and dried under vacuum to give 0.497 g (99%) of the title compound as a white solid.

$^1$H NMR (400 MHz, DMSO-$d_6$) δ 9.42, 8.62–8.64, 7.84, 7.64–7.69, 7.50–7.56, 7.18–7.22, 6.77, 3.69–3.74, 3.49–3.55, 3.22–3.28, 3.11–3.18, 2.29, 2.04–2.08, 1.98–2.03.

EXAMPLE 16

Preparation of 5-(1,4-diazepan-1-yl)-N,N-diethyl-2-[(3-fluorophenyl)sulfonyl]phenylamine

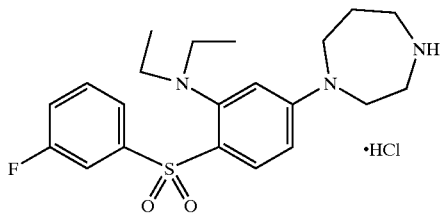

Following the general procedure of EXAMPLE 2 and making non critical variations, the title compound is obtained.

MS (CI) m/z 406 (MH$^+$), 408, 406, 249, 247, 245, 219, 69, 58, 56, 52.

EXAMPLE 17

Preparation of N-[5-(1,4-diazepan-1-yl)-2-(phenylsulfonyl) phenyl]acetamide

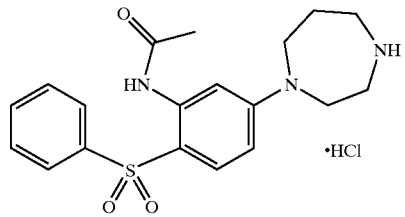

Following the general procedure of EXAMPLE 15 and making non critical variations but using fluorothiophenol as a starting material, the title compound is obtained.

HRMS (FAB) calcd for $C_{19}H_{23}N_3O_3S+H_1$ 374.1538, found 374.1515.

EXAMPLE 18

Preparation of N-[2-[(3-fluorophenyl)sulfonyl]-5-(4-methyl-1,4-diazepan-1-yl)phenyl]acetamide.

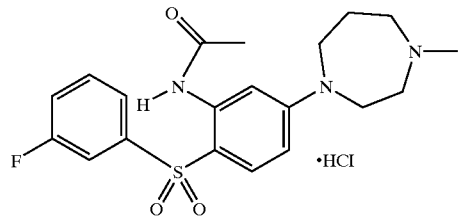

Following the general procedure of EXAMPLE 15 and making non critical variations, the title compound is obtained.

HRMS (FAB) calcd for $C_{20}H_{24}FN_3O_3S+H_1$ 406.1600, found 406.1602.

EXAMPLE 19

Preparation of N-[5-(1,4-diazepan-1-yl)-2-[(3-fluorophenyl) sulfonyl]phenyl]-N-ethylacetamide.

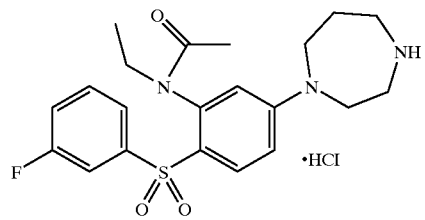

Following the general procedure of EXAMPLE 15 and making non critical variations, the title compound is obtained.

HRMS (FAB) calcd for $C_{21}H_{26}FN_3O_3S+H_1$ 420.1757, found 420.1760.

Following the general procedure of EXAMPLE 1–19 and making non critical variations, the following compounds can be obtained. Examples of these compounds are:
(1) 5-(1,4-diazepan-1-yl)-2-[(4-fluorophenyl)sulfonyl]phenylamine,
(2) 5-(1,4-diazepan-1-yl)-N-methyl-2-(phenylsulfonyl)phenylamine,
(3) 5-(1,4-diazepan-1-yl)-2-[(4-fluorophenyl)sulfonyl]-N-methylphenylamine,
(4) 5-(1,4-diazepan-1-yl)-2-[(3,4-difluorophenyl)sulfonyl]-N-methylphenylamine,
(5) 5-(1,4-diazepan-1-yl)-2-[(3,5-difluorophenyl)sulfonyl]-N-methylphenylamine,
(6) 5-(1,4-diazepan-1-yl)-N-ethyl-2-(phenylsulfonyl)phenylamine,
(7) 5-(1,4-diazepan-1-yl)-N-ethyl-2-[(4-fluorophenyl)sulfonyl]phenylamine,
(8) 5-(1,4-diazepan-1-yl)-N-ethyl-2-[(3,4-difluorophenyl)sulfonyl]phenylamine,
(9) 5-(1,4-diazepan-1-yl)-N-ethyl-2-[(3,5-difluorophenyl)sulfonyl]phenylamine,
(10) 5-(1,4-diazepan-1-yl)-2-(phenylsulfonyl)-N-propyl phenylamine,

(11) 5-(1,4-diazepan-1-yl)-2-[(3-fluorophenyl)sulfonyl]-N-propylphenylamine,
(12) 5-(1,4-diazepan-1-yl)-2-[(4-fluorophenyl)sulfonyl]-N-propylphenylamine,
(13) 5-(1,4-diazepan-1-yl)-2-[(3,4-difluorophenyl)sulfonyl]-N-propylphenylamine,
(14) 5-(1,4-diazepan-1-yl)-2-[(3,5-difluorophenyl)sulfonyl]-N-propylphenylamine,
(15) 5-(1,4-diazepan-1-yl)-N,N-dimethyl-2-(phenylsulfonyl)phenylamine,
(16) 5-(1,4-diazepan-1-yl)-2-[(3-fluorophenyl)sulfonyl]-N,N-dimethylphenylamine,
(17) 5-(1,4-diazepan-1-yl)-2-[(4-fluorophenyl)sulfonyl]-N,N-dimethylphenylamine,
(18) 5-(1,4-diazepan-1-yl)-2-[(3,4-difluorophenyl)sulfonyl]-N,N-dimethylphenylamine,
(19) 5-(1,4-diazepan-1-yl)-2-[(3,5-difluorophenyl)sulfonyl]-N,N-dimethylphenylamine,
(20) 5-(1,4-diazepan-1-yl)-N,N-diethyl-2-(phenylsulfonyl)phenylamine,
(21) 5-(1,4-diazepan-1-yl)-N,N-diethyl-2-[(4-fluorophenyl)sulfonyl]phenylamine,
(22) 5-(1,4-diazepan-1-yl)-N,N-diethyl-2-[(3,4-difluorophenyl)sulfonyl]phenylamine,
(23) 5-(1,4-diazepan-1-yl)-N,N-diethyl-2-[(3,5-difluorophenyl)sulfonyl]phenylamine,
(24) 5-(1,4-diazepan-1-yl)-2-(phenylsulfonyl)-N,N-dipropylphenylamine,
(25) 5-(1,4-diazepan-1-yl)-2-[(3-fluorophenyl)sulfonyl]-N,N-dipropylphenylamine,
(26) 5-(1,4-diazepan-1-yl)-2-[(4-fluorophenyl)sulfonyl]-N,N-dipropylphenylamine,
(27) 5-(1,4-diazepan-1-yl)-2-[(3,4-difluorophenyl)sulfonyl]-N,N-dipropylphenylamine, or (28) 5-(1,4-diazepan-1-yl)-2-[(3,5-difluorophenyl)sulfonyl]-N,N-dipropylphenylamine.

Another examples are:
(1) N-[5-(1,4-diazepan-1-yl)-2-[(4-fluorophenyl)sulfonyl]phenyl]acetamide,
(2) N-[5-(1,4-diazepan-1-yl)-2-[(3,4-difluorophenyl)sulfonyl]phenyl]acetamide,
(3) N-[5-(1,4-diazepan-1-yl)-2-[(3,5-difluorophenyl)sulfonyl]phenyl]acetamide,
(4) N-[5-(1,4-diazepan-1-yl)-2-(phenylsulfonyl)phenyl]-N-methylacetamide,
(5) N-5-(1,4-diazepan-1-yl)-2-[(3-fluorophenyl)sulfonyl]phenyl-N-methylacetamide,
(6) N-[5-(1,4-diazepan-1-yl)-2-[(4-fluorophenyl)sulfonyl]phenyl]-N-methylacetamide,
(7) N-[5-(1,4-diazepan-1-yl)-2-[(3,4-difluorophenyl)sulfonyl]phenyl]-N-methylacetamide,
(8) N-[5-(1,4-diazepan-1-yl)-2-[(3,5-difluorophenyl)sulfonyl]phenyl]-N-methylacetamide,
(9) N-[5-(1,4-diazepan-1-yl)-2-(phenylsulfonyl)phenyl]-N-ethylacetamide,
(10) N-[5-(1,4-diazepan-1-yl)-2-[(4-fluorophenyl)sulfonyl]phenyl]-N-ethylacetamide,
(11) N-[5-(1,4-diazepan-1-yl)-2-[(3,4-difluorophenyl)sulfonyl]phenyl]-N-ethylacetamide,
(12) N-[5-(1,4-diazepan-1-yl)-2-[(3,5-difluorophenyl)sulfonyl]phenyl]-N-ethylacetamide,
(13) N-[5-(1,4-diazepan-1-yl)-2-(phenylsulfonyl)phenyl]-N-propylacetamide,
(14) N-[5-(1,4-diazepan-1-yl)-2-[(3-fluorophenyl)sulfonyl]phenyl]-N-propylacetamide,
(15) N-[5-(1,4-diazepan-1-yl)-2-[(4-fluorophenyl)sulfonyl]phenyl]-N-propylacetamide,
(16) N-[5-(1,4-diazepan-1-yl)-2-[(3,4-difluorophenyl)sulfonyl]phenyl-N-propylacetamide,
(17) N-[5-(1,4-diazepan-1-yl)-2-[(3,5-difluorophenyl)sulfonyl]phenyl]-N-propylacetamide,
(18) N-[5-(4-methyl-1,4-diazepan-1-yl)-2-(phenylsulfonyl)phenyl]acetamide,
(19) N-[2-[(4-fluorophenyl)sulfonyl]-5-(4-methyl-1,4-diazepan-1-yl)-phenyl]acetamide,
(20) N-[2-[(3,4-difluorophenyl)sulfonyl]-5-(4-methyl-1,4-diazepan-1-yl)phenyl]acetamide,
(21) N-[2-[(3,5-difluorophenyl)sulfonyl-5-(4-methyl-1,4-diazepan-1-yl)phenyl]acetamide,
(22) N-methyl-N-[5-(4-methyl-1,4-diazepan-1-yl)-2-(phenylsulfonyl)phenyl]acetamide,
(23) N-[2-[(3-fluorophenyl)sulfonyl]-5-(4-methyl-1,4-diazepan-1-yl)phenyl]-N-methylacetamide,
(24) N-[2-[(4-fluorophenyl)sulfonyl]-5-(4-methyl-1,4-diazepan-1-yl)phenyl]-N-methylacetamide,
(25) N-[2-[(3,4-difluorophenyl)sulfonyl]-5-(4-methyl-1,4-diazepan-1-yl)phenyl]-N-methylacetamide,
(26) N-[2-[(3,5-difluorophenyl)sulfonyl]-5-(4-methyl-1,4-diazepan-1-yl)phenyl]-N-methylacetamide,
(27) N-ethyl-N-[5-(4-methyl-1,4-diazepan-1-yl)-2-(phenylsulfonyl)phenylacetamide,
(28) N-ethyl-N-[2-[(3-fluorophenyl)sulfonyl]-5-(4-methyl-1,4-diazepan-1-yl)phenyl]acetamide,
(29) N-ethyl-N-[2-[(4-fluorophenyl)sulfonyl]-5-(4-methyl-1,4-diazepan-1-yl)phenyl]acetamide,
(30) N-ethyl-N-[2-[(3,4-difluorophenyl)sulfonyl]-5-(4-methyl-1,4-diazepan-1-yl)phenyl]acetamide,
(31) N-ethyl-N-[2-[(3,5-difluorophenyl)sulfonyl]-5-(4-methyl-1,4-diazepan-1-yl)phenyl]acetamide,
(32) N-[5-(4-methyl-1,4-diazepan-1-yl)-2-(phenylsulfonyl)phenyl]-N-propylacetamide,
(33) N-[2-[(3-fluorophenyl)sulfonyl]-5-(4-methyl-1,4-diazepan-1-yl)phenyl]-N-propylacetamide,
(34) N-[2-[(4-fluorophenyl)sulfonyl]-5-(4-methyl-1,4-diazepan-1-yl)phenyl]-N-propylacetamide,
(35) N-[2-[(3,4-difluorophenyl)sulfonyl]-5-(4-methyl-1,4-diazepan-1-yl)phenyl]-N-propylacetamide,
(36) N-[2-[(3,5-difluorophenyl)sulfonyl]-5-(4-methyl-1,4-diazepan-1-yl)phenyl]-N-propylacetamide, Another examples are:
(1) 5-(4-methyl-1,4-diazepan-1-yl)-2-(phenylsulfonyl)phenylamine,
(2) 2-[(3-fluorophenyl)sulfonyl]-5-(4-methyl-1,4-diazepan-1-yl)phenylamine,
(3) 2-[(4-fluorophenyl)sulfonyl]-5-(4-methyl-1,4-diazepan-1-yl)phenylamine,
(4) 2-[(3,4-difluorophenyl)sulfonyl]-5-(4-methyl-1,4-diazepan-1-yl)phenylamine,
(5) 2-[(3,5-difluorophenyl)sulfonyl]-5-(4-methyl-1,4-diazepan-1-yl)phenylamine,
(6) N-methyl-N-[5-(4-methyl-1,4-diazepan-1-yl)-2-(phenylsulfonyl)phenyl]amine,
(7) N-[2-[(3-fluorophenyl)sulfonyl]-5-(4-methyl-1,4-diazepan-1-yl)phenyl]-N-methylamine,
(8) N-[2-[(4-fluorophenyl)sulfonyl]-5-(4-methyl-1,4-diazepan-1-yl)phenyl]-N-methyl amine,
(9) N-[2-[(3,4-difluorophenyl)sulfonyl]-5-(4-methyl-1,4-diazepan-1-yl)phenyl]-N-methylamine,
(10) N-[2-[(3,5-difluorophenyl)sulfonyl]-5-(4-methyl-1,4-diazepan-1-yl)phenyl]-N-methylamine,
(11) N-ethyl-N-[5-(4-methyl-1,4-diazepan-1-yl)-2-(phenylsulfonyl)phenyl]amine,
(12) N-ethyl-N-[2-[(3-fluorophenyl)sulfonyl]-5-(4-methyl-1,4-diazepan-1-yl)phenyl]amine,

(13) N-ethyl-N-[2-[(4-fluorophenyl)sulfonyl]-5-(4-methyl-1,4-diazepan-1-yl)phenyl]amine,
(14) N-ethyl-N-[2-[(3,4-difluorophenyl)sulfonyl]-5-(4-methyl-1,4-diazepan-1-yl)phenyl]amine,
(15) N-ethyl-N-[2-[(3,5-difluorophenyl)sulfonyl]-5-(4-methyl-1,4-diazepan-1-yl)phenyl]amine,
(16) N-[5-(4-methyl-1,4-diazepan-1-yl)-2-(phenylsulfonyl)phenyl]-N-propylamine,
(17) N-[2-[(3-fluorophenyl)sulfonyl]-5-(4-methyl-1,4-diazepan-1-yl)phenyl]-N-propylamine,
(18) N-[2-[(4-fluorophenyl)sulfonyl]-5-(4-methyl-1,4-diazepan-1-yl)phenyl]-N-propylamine,
(19) N-[2-[(3,4-difluorophenyl)sulfonyl]-5-(4-methyl-1,4-diazepan-1-yl)phenyl]-N-propylamine,
(20) N-[2-[(3,5-difluorophenyl)sulfonyl]-5-(4-methyl-1,4-diazepan-1-yl)phenyl]-N-propylamine,
(21) N,N-dimethyl-N-[5-(4-methyl-1,4-diazepan-1-yl)-2-(phenylsulfonyl)phenyl]amine,
(22) N-[2-[(3-fluorophenyl)sulfonyl]-5-(4-methyl-1,4-diazepan-1-yl)phenyl]-N,N-dimethylamine,
(23) N-[2-[(4-fluorophenyl)sulfonyl]-5-(4-methyl-1,4-diazepan-1-yl)phenyl]-N,N-dimethylamine,
(24) N-[2-[(3,4-difluorophenyl)sulfonyl]-5-(4-methyl-1,4-diazepan-1-yl)phenyl]-N,N-dimethylamine,
(25) N-[2-[(3,5-difluorophenyl)sulfonyl]-5-(4-methyl-1,4-diazepan-1-yl)phenyl]-N,N-dimethylamine,
(26) N,N-diethyl-N-[5-(4-methyl-1,4-diazepan-1-yl)-2-(phenylsulfonyl)phenyl]amine,
(27) N,N-diethyl-N-[2-[(3-fluorophenyl)sulfonyl]-5-(4-methyl-1,4-diazepan-1-yl)phenyl]amine,
(28) N,N-diethyl-N-[2-[(4-fluorophenyl)sulfonyl]-5-(4-methyl-1,4-diazepan-1-yl)phenyl]amine,
(29) N,N-diethyl-N-[2-[(3,4-difluorophenyl)sulfonyl]-5-(4-methyl-1,4-diazepan-1-yl)phenyl]amine,
(30) N,N-diethyl-N-[2-[(3,5-difluorophenyl)sulfonyl]-5-(4-methyl-1,4-diazepan-1-yl)phenyl]amine,
(31) N-[5-(4-methyl-1,4-diazepan-1-yl)-2-(phenylsulfonyl)phenyl]-N,N-dipropylamine,
(32) N-[2-[(3-fluorophenyl)sulfonyl]-5-(4-methyl-1,4-diazepan-1-yl)phenyl]-N,N-dipropylamine,
(33) N-[2-[(4-fluorophenyl)sulfonyl]-5-(4-methyl-1,4-diazepan-1-yl)phenyl]-N,N-dipropylamine,
(34) N-[2-[(3,4-difluorophenyl)sulfonyl]-5-(4-methyl-1,4-diazepan-1-yl)phenyl]-N,N-dipropylamine, or
(35) N-[2-[(3,5-difluorophenyl)sulfonyl]-5-(4-methyl-1,4-diazepan-1-yl)phenyl-N,N-dipropylamine.

Another examples are:
(1) 2-[(3-fluorophenyl)sulfonyl]-5-(1-piperazinyl)phenylamine,
(2) 2-[(3,4-difluorophenyl)sulfonyl]-5-(1-piperazinyl)phenylamine,
(3) 2-[(3,5-difluorophenyl)sulfonyl]-5-(1-piperazinyl)phenylamine,
(4) N-methyl-2-(phenylsulfonyl)-5-(1-piperazinyl)phenylamine,
(5) 2-[(3-fluorophenyl)sulfonyl]-N-methyl-5-(1-piperazinyl)phenylamine,
(6) 2-[(3,4-difluorophenyl)sulfonyl]-N-methyl-5-(1-piperazinyl)phenylamine,
(7) 2-[(3,5-difluorophenyl)sulfonyl]-N-methyl-5-(1-piperazinyl)phenylamine,
(8) N-ethyl-2-[(4-fluorophenyl)sulfonyl]-5-(1-piperazinyl)phenylamine,
(9) N-ethyl-2-[(3,4-difluorophenyl)sulfonyl]-5-(1-piperazinyl)phenylamine,
(10) N-ethyl-2-[(3,5-difluorophenyl)sulfonyl]-5-(1-piperazinyl)phenyl amine,
(11) 2-(phenylsulfonyl)-5-(1-piperazinyl)-N-propylphenylamine,
(12) 2-[(3-fluorophenyl)sulfonyl]-5-(1-piperazinyl)-N-propylphenylamine,
(13) 2-[(4-fluorophenyl)sulfonyl]-5-(1-piperazinyl)-N-propylphenylamine,
(14) 2-[(3,4-difluorophenyl)sulfonyl]-5-(1-piperazinyl)-N-propylphenylamine,
(15) 2-[(3,5-difluorophenyl)sulfonyl]-5-(1-piperazinyl)-N-propylphenylamine,
(16) N,N-dimethyl-2-(phenylsulfonyl)-5-(1-piperazinyl)phenylamine,
(17) 2-[(3-fluorophenyl)sulfonyl]-N,N-dimethyl-5-(1-piperazinyl)phenylamine,
(18) 2-[(4-fluorophenyl)sulfonyl]-N,N-dimethyl-5-(1-piperazinyl)phenylamine,
(19) 2-[(3,4-difluorophenyl)sulfonyl]-N,N-dimethyl-5-(1-piperazinyl)phenylamine,
(20) 2-[(3,5-difluorophenyl)sulfonyl]-N,N-dimethyl-5-(1-piperazinyl)phenylamine,
(21) N,N-diethyl-2-(phenylsulfonyl)-5-(1-piperazinyl)phenylamine,
(22) N,N-diethyl-2-[(3-fluorophenyl)sulfonyl]-5-(1-piperazinyl)phenylamine,
(23) N,N-diethyl-2-[(4-fluorophenyl)sulfonyl]-5-(1-piperazinyl)phenylamine,
(24) N,N-diethyl-2-[(3,4-difluorophenyl)sulfonyl]-5-(1-piperazinyl)phenylamine,
(25) N,N-diethyl-2-[(3,5-difluorophenyl)sulfonyl]-5-(1-piperazinyl)phenylamine,
(26) 2-(phenylsulfonyl)-5-(1-piperazinyl)-N,N-dipropylphenylamine,
(27) 2-[(3-fluorophenyl)sulfonyl]-5-(1-piperazinyl)-N,N-dipropylphenylamine,
(28) 2-[(4-fluorophenyl)sulfonyl]-5-(1-piperazinyl)-N,N-dipropylphenylamine,
(29) 2-[(3,4-difluorophenyl)sulfonyl]-5-(1-piperazinyl)-N,N-dipropylphenylamine,
or
(30) 2-[(3,5-difluorophenyl)sulfonyl]-5-(1-piperazinyl)-N,N-dipropylphenylamine.

Another examples are:
(1) N-[2-(phenylsulfonyl)-5-(1-piperazinyl)phenyl]acetamide,
(2) N-[2-[(3-fluorophenyl)sulfonyl]-5-(1-piperazinyl)phenyl]acetamide,
(3) N-[2-[(4-fluorophenyl)sulfonyl]-5-(1-piperazinyl)phenyl]acetamide,
(4) N-[2-[(3,4-difluorophenyl)sulfonyl]-5-(1-piperazinyl)phenyl]acetamide,
(5) N-[2-[(3,5-difluorophenyl)sulfonyl]-5-(1-piperazinyl)phenyl]acetamide,
(6) N-methyl-N-[2-(phenylsulfonyl)-5-(1-piperazinyl)phenyl]acetamide,
(7) N-[2-[(3-fluorophenyl)sulfonyl]-5-(1-piperazinyl)phenyl]-N-methylacetamide,
(8) N-[2-[(4-fluorophenyl)sulfonyl]-5-(1-piperazinyl)phenyl]-N-methylacetamide,
(9) N-[2-[(3,4-difluorophenyl)sulfonyl]-5-(1-piperazinyl)phenyl]-N-methylacetamide,
(10) N-[2-[(3,5-difluorophenyl)sulfonyl]-5-(1-piperazinyl)phenyl]-N-methylacetamide,
(11) N-ethyl-N-[2-(phenylsulfonyl)-5-(1-piperazinyl)phenyl]acetamide,
(12) N-ethyl-N-[2-[(3-fluorophenyl)sulfonyl]-5-(1-piperazinyl)phenyl]acetamide,
(13) N-ethyl-N-[2-[(4-fluorophenyl)sulfonyl]-5-(1-piperazinyl)phenyl]acetamide,

(14) N-ethyl-N-[2-[(3,4-difluorophenyl)sulfonyl]-5-(1-piperazinyl)phenyl]acetamide,
(15) N-ethyl-N-[2-[(3,5-difluorophenyl)sulfonyl]-5-(1-piperazinyl)phenyl]acetamide,
(16) N-[2-(phenylsulfonyl)-5-(1-piperazinyl)phenyl]-N-propylacetamide,
(17) N-[2-[(3-fluorophenyl)sulfonyl]-5-(1-piperazinyl)phenyl]-N-propylacetamide,
(18) N-[2-[(4-fluorophenyl)sulfonyl]-5-(1-piperazinyl)phenyl]-N-propylacetamide,
(19) N-[2-[(3,4-difluorophenyl)sulfonyl]-5-(1-piperazinyl)phenyl]-N-propylacetamide,
(20) N-[2-[(3,5-difluorophenyl)sulfonyl]-5-(1-piperazinyl)phenyl]-N-propylacetamide,
(21) N-[5-(4-methyl-1-piperazinyl)-2-(phenylsulfonyl)phenyl]acetamide,
(22) N-[2-[(3-fluorophenyl)sulfonyl]-5-(4-methyl-1-piperazinyl)phenyl]acetamide,
(23) N-[2-[(4-fluorophenyl)sulfonyl]-5-(4-methyl-1-piperazinyl)phenyl]acetamide,
(24) N-[2-[(3,4-difluorophenyl)sulfonyl]-5-(4-methyl-1-piperazinyl)phenyl]acetamide,
(25) N-[2-[(3,5-difluorophenyl)sulfonyl-5-(4-methyl-1-piperazinyl)phenyl]acetamide,
(26) N-methyl-N-[5-(4-methyl-1-piperazinyl)-2-(phenylsulfonyl)phenyl]acetamide,
(27) N-[2-[(3-fluorophenyl)sulfonyl]-5-(4-methyl-1-piperazinyl)phenyl]-N-methylacetamide,
(28) N-[2-[(4-fluorophenyl)sulfonyl]-5-(4-methyl-1-piperazinyl)phenyl]-N-methylacetamide,
(29) N-[2-[(3,4-difluorophenyl)sulfonyl]-5-(4-methyl-1-piperazinyl)phenyl]-N-methylacetamide,
(30) N-[2-[(3,5-difluorophenyl)sulfonyl]-5-(4-methyl-1-piperazinyl)phenyl]-N-methylacetamide,
(31) N-ethyl-N-[5-(4-methyl-1-piperazinyl)-2-(phenylsulfonyl)phenyl]acetamide,
(32) N-ethyl-N-[2-[(3-fluorophenyl)sulfonyl]-5-(4-methyl-1-piperazinyl)phenyl]acetamide,
(33) N-ethyl-N-[2-[(4-fluorophenyl)sulfonyl]-5-(4-methyl-1-piperazinyl)phenyl]acetamide,
(34) N-ethyl-N-[2-[(3,4-difluorophenyl)sulfonyl]-5-(4-methyl-1-piperazinyl)phenyl]-N-ethyl acetamide,
(35) N-ethyl-N-[2-[(3,5-difluorophenyl)sulfonyl]-5-(4-methyl-1-(36) piperazinyl)phenyl]acetamide,
(36) N-[5-(4-methyl-1-piperazinyl)-2-(phenylsulfonyl)phenyl]-N-propylacetamide,
(37) N-[2-[(3-fluorophenyl)sulfonyl]-5-(4-methyl-1-piperazinyl)phenyl]-N-propylacetamide,
(38) N-[2-[(4-fluorophenyl)sulfonyl]-5-(4-methyl-1-piperazinyl)phenyl]-N-propylacetamide,
(39) N-[2-[(3,4-difluorophenyl)sulfonyl]-5-(4-methyl-1-piperazinyl)phenyl]-N-propylacetamide, or
(40) N-[2-[(3,5-difluorophenyl)sulfonyl]-5-(4-methyl-1-piperazinyl)phenyl]-N-propylacetamide.

Another examples are:
(1) 2-[(3,4-difluorophenyl)sulfonyl]-5-(4-methyl-1-piperazinyl)phenylamine,
(2) 2-[(3,5-difluorophenyl)sulfonyl]-5-(4-methyl-1-piperazinyl)phenylamine,
(3) N-methyl-N-[5-(4-methyl-1-piperazinyl)-2-(phenylsulfonyl)phenyl]amine,
(4) N-[2-[(3-fluorophenyl)sulfonyl]-5-(4-methyl-1-piperazinyl)phenyl]-N-methylamine,
(5) N-[2-[(4-fluorophenyl)sulfonyl]-5-(4-methyl-1-piperazinyl)phenyl]-N-methylamine,
(6) N-[2-[(3,4-difluorophenyl)sulfonyl]-5-(4-methyl-1-piperazinyl)phenyl]-N-methylamine,
(7) N-[2-[(3,5-difluorophenyl)sulfonyl]-5-(4-methyl-1-piperazinyl)phenyl]-N-methylamine,
(8) N-ethyl-N-[5-(4-methyl-1-piperazinyl)-2-(phenylsulfonyl)phenyl]amine,
(9) N-ethyl-N-[2-[(3-fluorophenyl)sulfonyl]-5-(4-methyl-1-piperazinyl)phenyl]amine,
(10) N-ethyl-N-[2-[(4-fluorophenyl)sulfonyl]-5-(4-methyl-1-piperazinyl)phenyl]amine,
(11) N-ethyl-N-[2-[(3,4-difluorophenyl)sulfonyl]-5-(4-methyl-1-piperazinyl)phenyl]amine,
(12) N-ethyl-N-[2-[(3,5-difluorophenyl)sulfonyl]-5-(4-methyl-1-piperazinyl)phenyl]amine,
(13) N-[5-(4-methyl-1-piperazinyl)-2-(phenylsulfonyl)phenyl]-N-propylamine,
(14) N-[2-[(3-fluorophenyl)sulfonyl]-5-(4-methyl-1-piperazinyl)phenyl]-N-propylamine,
(15) N-[2-[(4-fluorophenyl)sulfonyl]-5-(4-methyl-1-piperazinyl)phenyl]-N-propylamine,
(16) N-[2-[(3,4-difluorophenyl)sulfonyl]-5-(4-methyl-1-piperazinyl)phenyl]-N-propylamine,
(17) N-[2-[(3,5-difluorophenyl)sulfonyl]-5-(4-methyl-1-piperazinyl)phenyl]-N-propylamine,
(18) N,N-dimethyl-N-[5-(4-methyl-1-piperazinyl)-2-(phenylsulfonyl)phenyl]amine,
(19) N-[2-[(3-fluorophenyl)sulfonyl]-5-(4-methyl-1-piperazinyl)phenyl]-N,N-dimethylamine,
(20) N-[2-[(4-fluorophenyl)sulfonyl]-5-(4-methyl-1-piperazinyl)phenyl]-N,N-dimethylamine,
(21) N-[2-[(3,4-difluorophenyl)sulfonyl]-5-(4-methyl-1-piperazinyl)phenyl]-N,N-dimethylamine,
(22) N-[2-[(3,5-difluorophenyl)sulfonyl]-5-(4-methyl-1-piperazinyl)phenyl]-N,N-dimethylamine,
(23) N,N-diethyl-N-[5-(4-methyl-1-piperazinyl)-2-(phenylsulfonyl)phenyl]amine,
(24) N,N-diethyl-N-[2-[(3-fluorophenyl)sulfonyl]-5-(4-methyl-1-piperazinyl)phenyl]amine,
(25) N,N-diethyl-N-[2-[(4-fluorophenyl)sulfonyl]-5-(4-methyl-1-piperazinyl)phenyl]amine,
(26) N,N-diethyl-N-[2-[(3,4-difluorophenyl)sulfonyl]-5-(4-methyl-1-piperazinyl)phenyl]amine,
(27) N,N-diethyl-N-[2-[(3,5-difluorophenyl)sulfonyl]-5-(4-methyl-1-piperazinyl)phenyl]amine,
(28) N-[5-(4-methyl-1-piperazinyl)-2-(phenylsulfonyl)phenyl]-N,N-dipropylamine,
(29) N-[2-[(3-fluorophenyl)sulfonyl]-5-(4-methyl-1-piperazinyl)phenyl]-N,N-dipropylamine,
(30) N-[2-[(4-fluorophenyl)sulfonyl]-5-(4-methyl-1-piperazinyl)phenyl]-N,N-dipropylamine,
(31) N-[2-[(3,4-difluorophenyl)sulfonyl]-5-(4-methyl-1-piperazinyl)phenyl]-N,N-dipropylamine, or
(32) N-[2-[(3,5-difluorophenyl)sulfonyl]-5-(4-methyl-1-piperazinyl)phenyl-N,N-dipropylamine.

What is claimed is:
1. A compound selected from the group consisting of 5-(1,4-diazepan-1-yl)-2-[(3-fluorophenyl) sulfonyl] phenylamine; 5-(1,4-diazepan-1-yl)-N-ethyl-2-[(3-fluorophenyl) sulfonyl]aniline; N-[5-(1,4-diazepan-1-yl)-2-[(3-fluorophenyl)sulfonyl]phenyl]acetamide; N-[5-(1,4-diazepan-1-yl)-2-[phenylsulfonyl]phenyl]acetamide; and pharmaceutically acceptable salts thereof, wherein the compound includes an isotopic label.
2. The compound of claim 1, wherein the compound includes at least on atom selected from Carbon-11, Nitrogen-13, Oxygen-15, and Fluorine-18.

3. A method of performing positron emission tomography comprising:

incorporating an isotopically labeled compound into tissue of a mammal, wherein the isotopically labeled compound is selected from 5-(1,4-diazepan-1-yl)-2-[(3-fluorophenyl) sulfonyl]phenylamine; 5-(1,4-diazepan-1-yl)-N-ethyl-2-[(3-fluorophenyl) sulfonyl] aniline; N-[5-(1,4-diazepan-1-yl)-2-[(3-fluorophenyl) sulfonyl]phenyl]acetamide; N-[5-(1,4-diazepan-1-yl)-2-[phenylsulfonyl]phenyl]acetamide; and pharmaceutically acceptable salts thereof, and each compound includes at least one atom selected from Carbon-11, Nitrogen-13, Oxygen-15, and Fluorine-18.

4. A method of performing nuclear magnetic resonance imaging comprising:

incorporating a compound into tissue of a mammal, wherein the compound is selected from the group consisting of 5-(1,4-diazepan-1-yl)-2-[(3-fluorophenyl) sulfonyl]phenylamine; 5-(1,4-diazepan-1-yl)-N-ethyl-2-[(3-fluorophenyl) sulfonyl]aniline; N-[5-(1,4-diazepan-1-yl)-2-[(3-fluorophenyl)sulfonyl]phenyl] acetamide; and pharmaceutically acceptable salts thereof, provided that the fluorine atom is $^{19}$F.

* * * * *